United States Patent
Zhao et al.

(10) Patent No.: US 8,809,300 B2
(45) Date of Patent: Aug. 19, 2014

(54) **DEPOLYMERIZED GLYCOSAMINOGLYCAN FROM *THELENOTA ANANAS* AND PREPARATION METHOD THEREOF**

(75) Inventors: Jinhua Zhao, Shenzhen (CN); Hui Kang, Shenzhen (CN); Mingyi Wu, Shenzhen (CN); Weizhen Zeng, Shenzhen (CN); Zi Li, Shenzhen (CN); Yuan Gao, Shenzhen (CN); Jing Cui, Shenzhen (CN); Zhiguo Wang, Shenzhen (CN); Hanlin Feng, Shenzhen (CN); Lin Yu, Shenzhen (CN)

(73) Assignee: Shenzhen Neptunus Pharmaceutical Co., Ltd., Guangdong (CN)

( * ) Notice: Subject to any disclaimer, the term of this patent is extended or adjusted under 35 U.S.C. 154(b) by 0 days.

(21) Appl. No.: 13/512,142

(22) PCT Filed: Oct. 25, 2010

(86) PCT No.: PCT/CN2010/001678
§ 371 (c)(1),
(2), (4) Date: Jun. 29, 2012

(87) PCT Pub. No.: WO2011/063595
PCT Pub. Date: Jun. 3, 2011

(65) Prior Publication Data
US 2012/0270834 A1    Oct. 25, 2012

(30) Foreign Application Priority Data

Nov. 25, 2009    (CN) .......................... 2009 1 0109861

(51) Int. Cl.
| | | |
|---|---|---|
| *A61K 31/726* | (2006.01) | |
| *A61K 31/715* | (2006.01) | |
| *C08B 37/00* | (2006.01) | |
| *C07H 5/06* | (2006.01) | |
| *A61P 7/02* | (2006.01) | |
| *A61K 31/737* | (2006.01) | |

(52) U.S. Cl.
CPC ............. *A61K 31/737* (2013.01); *A61K 31/726* (2013.01); *C08B 37/0063* (2013.01)
USPC ............. 514/54; 536/54; 536/122; 536/55.1; 536/123.1; 536/53

(58) Field of Classification Search
USPC ............. 514/54; 536/54, 122, 55.1, 123.1, 53
See application file for complete search history.

(56) References Cited

U.S. PATENT DOCUMENTS 5,993,797 A * 11/1999 Kitazato et al. ............... 424/78.3
2004/0087543 A1    5/2004 Shriver et al.

FOREIGN PATENT DOCUMENTS

| CN | 1651470 A | 8/2005 |
|---|---|---|
| CN | 101057859 A | 10/2007 |
| CN | 101451157 A | 6/2009 |
| CN | 101724086 A | 6/2010 |
| JP | 2007008899 A | 1/2007 |

OTHER PUBLICATIONS

Nagase et al. (J. Biochem. (1996), 119, pp. 63-69).*

* cited by examiner

*Primary Examiner* — Shaojia Anna Jiang
*Assistant Examiner* — Michael C Henry
(74) *Attorney, Agent, or Firm* — Cesari and McKenna, LLP

(57) ABSTRACT

Disclosed is a depolymerized glycosaminoglycan from *Thelenota ananas* (dTHG), weight average molecular weight of which is about 8000~20000 Da, and monosaccharide components of which are acetylgalactosamine (GalNAc), glucuronic acid (GlcUA), fucose (Fuc) or their sulfates (expressed as —$OSO_3^-$), in which molar ratio of GalNAc:GlcUA:Fuc:—$OSO_3^-$ is about 1:(1±0.3):(1±0.3):(3.5±0.5). Said dTHG is a potent endogenous inhibitor of factor X, which has good anticoagulant and antithrombotic activity, and can be used for the prevention and/or treatment of thrombotic diseases. Also provided is a method for preparing said dTHG, which comprises steps of 1) extracting and obtaining fucosylated glycosaminoglycan (THG) from the body wall of *Thelenota ananas*; 2) depolymerizing THG to obtain dTHG by method of peroxide depolymerization or method of peroxide depolymerization catalyzed by catalyst of the fourth period transition metal ions; 3) removing impurities with lower and/or higher molecular weight in dTHG.

20 Claims, 5 Drawing Sheets

DEPOLYMERIZED GLYCOSAMINOGLYCAN FROM *THELENOTA ANANAS* AND PREPARATION METHOD THEREOF

CROSS-REFERENCE TO RELATED APPLICATIONS

This application is the National Stage of International Application No. PCT/CN2010/001678, filed on Oct. 25, 2010, which claims the benefit of the priority date of Chinese Patent Application No. 200910109861.2 filed Nov. 25, 2009. The content of these applications is hereby incorporated by reference in its entirety.

FIELD OF THE INVENTION

The present invention relates to the field of medical technology, and particularly to a depolymerized glycosaminoglycan from *Thelenota ananas* and a preparation method of the same, a pharmaceutical composition containing the same and use of the same in preventing and/or treating thrombotic diseases. The present invention is a further invention based on Chinese patent application No. 200910110114.0 entitled "Depolymerized Fucosylated Glycosaminoglycan and Preparation Method of the same" filed by the same applicant on Nov. 6, 2009, the entire content of such application is incorporated herein by reference.

BACKGROUND OF THE INVENTION

Fucose-branched glycosaminoglycan (fucosylated glycosaminoglycan or fucose-containing glycos-aminoglycan, FGAG), also referred to as fucose-branched chondroitin sulfate (FCS), is a special glycosaminoglycan having sulfated fucose substituents extracted from the body wall or viscera of an echinoderm (Huizeng Fan, et al., *Pharmaceutical Journal*, 1980, 18(3): 203; Ricardo P. et al., *J. Biol. Chem.*, 1988, 263 (34): 18176; Yutaka K. et al., *J. Biol. Clem.*, 1990, 265:5081).

The existing literature shows that FGAG from sea cucumber have both common properties and differences. First, FGAG from different sources and prepared by different methods have some common features, i.e., FGAG has monosaccharide components including N-acetyl-galactosyl (GalNAc, A, chemical name of said N-acetyl-galactose is N-acetyl-2-deoxy-2-galactosamine, hereafter the same), glucuronosyl (GlcUA, U), fucosyl (Fuc, F) and their sulphate (see above reference of Huizeng Fan, 1980; Ricardo P, 1988; and Ken-ichiro Y. et al., *Tetrahedron Letters*, 1992, 33(34): 4959). In which, GlcUA and GalNAc (or its sulphate) interconnects through β (1-3) and β (1-4) glycosidic bonds to form a backbone, which is similar to a [GlcUA β(1-3)-GalNAc β(1-4)-] disaccharide repeating structural unit of chondroitin sulfate, while fucose or its sulfate attached to the backbone as a branch.

FGAG from different sources and prepared by different methods have chemical structural differences to varying degrees, for example:

(1) Difference in monosaccharide component ratio. FGAG from different sea cucumber species, from different tissues and even prepared by different methods may have significant difference in monosaccharide components. The monosaccharide components of FGAG from several sources are shown in Table 1.

TABLE 1

Monosaccharide components and their sulfate groups of FGAG from several sea cucumber

| Sources Sea cucumber species | Tissues | Chemical components (molar ratio) A:U:F:—OSO$_3^-$ | References |
|---|---|---|---|
| *Stichopus Japonicus* | body wall | 1:1.14:0.97:4.20 | Huizeng Fan, *Pharmaceutical Journal*, 1980, 15: 267 |
| | | 1:0.88:0.93:4.01 | Ken-ichiro Y, *Tetrahedron Letters*, 1992, 33: 4959 |
| | | 1:1.18:2.78:5.46 | Yutaka K, J. *Biol. Chem.*, 1990, 265: 5081 |
| | | 1:0.84:2.38:3.69[b] | Yutaka K. *Biochem. J.*, 2002, 132: 335 |
| | viscera | 1:1.00:1.00:4.70 | Huizeng Fan, *marine drugs*, 1983, (3): 134 |
| *Stichopus variegatus* | body wall | 1:1.21:1.29:4.62 | Judi Chen, *Chinese Journal of Marine Drugs*, 1994, (1): 24 |
| *Holothuria leucospilota* | body wall | 1:0.94:0.84:3.60 | Huizeng Fan, *Pharmaceutical Journal*. 1983, 18 (3): 203 |
| | | 1:0.96:0.78:1.98 | Haitang Li, *Journal of Chinese Medicinal Materials*, 1999, 22(7): 328 |
| *Holothuria atra* | body wall | 1:1.15:0.79:2.7[c] | Xiaoli Tang, *Journal of Chinese Medicinal Materials*, 1999, 22(5): 223 |
| *Holothuria scabr* | body wall | 1:1.28:0.68:1.72 | Jian Chen, Food and Fermentation Industries, 2006, 32: 123 |
| *Ludwigothurea grisea* | body wall | 1:1.17:2.17:2.39[c] | Paulo AS, Eur. *J. Biochem.*, 1987, 166: 639 |
| | | 1:0.90:0.97:2.67[d] | Ricardo PV, *J. Biol. Chem.*, 1988, 263: 18176 |
| | | 1:0.92:1.23:2.21 | Paulo AS, *J. Biol. Chem.*, 1996, 271: 23973 |

[a]expressed as mmol/g in the reference (0.81:0.69:1.93:2.99);
[b]expressed as wt % in the reference (16.2:20.3:11.66:23.52);
[c]expressed as 0.46:0.54:1.00:1.10 in the reference;
[d]expressed as 0.33:0.30:0.32:0.88 in the reference.

The difference between the components of FGAG obtained from different species, tissue origins and different extraction methods mainly lies in the larger change in the ratio of Fuc to sulfate group. It can be judged based on the data that not only different specie sources result in different FGAG, but also different extraction methods may lead to a larger difference in components of the product. For example, Yutaka K al. (1990, 2002), Huizeng Fan et al. (1980) and Ken-ichiro Y et. al (1992) respectively extracted FGAG from the body wall of *Stichopus Japonicus*, however the molar ratio of fucose in FGAG obtained by the former was 2 to 3 times higher than that of the tatters; while FGAG extracted from the same sea cucumber species (*L. grisea*) by the same research group also have larger differences in the ratio of fucose component (Paulo A S et al., 1987, 1988). FGAG obtained from the same tissue by different extraction method/time have different ratios of fucose component, it is probably because there exists non-GAG like fucosan pollution in FGAG product with higher ratio of fucose component, or there exists damage and loss of branch groups during the production of FGAG product with lower ratio of fucose component; in addition, it is probably related to the accuracy of content determination method.

(2) Difference in structure of backbone: As there are differences in the position and number of sulfate groups of such as chondroitin sulfate A, C and D, the differences in the position and number of sulfate groups also exist in the backbone of FGAF from different species. For example, the data show that GalNAc on the backbone of FGAG from *Stichopus japonicas* is sulfated at both 4- and 6-positions (Ken-ichiro Y et al., *Tetrahedron Letters*, 1992, 33: 4959); GalNAc on the backbone of FGAG from *Holothuria leucospilota* is sulfated only at 6-position but not 4-position (Huizeng Fan, *Pharmaceutical Journal*, 1983, 18 (3): 203); and on the backbone of FGAG from *L. grisea*, about 53% of the GalNAc are 6-sulfated, and small amounts of 4,6-sulfated (about 12%), 4-sulfated (about 4%) and nonsulfated (31%) are found (Lubor Borsig et al. *J. Biol. Chem.* 2007, 282: 14984).

(3) Difference in fucose residues on branch and their sulfation degree. Data show that FGAG from both *S. Japonicus* and *L. grisea* have three types of fucose residue branches, i.e., 2,4-disulfated, 3,4-disulfated, and 4-monosulfated fucoses; and the latter has about 25% of nonsulfated fucose residues, which occur as a cluster at the reducing end of FGAG (Ken-ichiro Y. et al., *Tetrahedron Letters*, 1992, 33: 4959, Paulo A S. et al., *J. Biol. Chem.*, 1996, 271: 23973).

As shown in Table 1, FGAG from *Stichopus japonicus* and *Stichopus variegates* generally show a higher degree of sulfation, while FGAG from *L. grisea*, *Holothuria atra*, and *Holothuria scabr* show lower degree of sulfation.

The existing data shows that FGAG from echinoderm has various biological activities.

Most FGAG from various sources has certain anticoagulant activity (Huizeng Fan, *Pharmaceutical Journal*, 1980, 15(5): 263; Peiwen Zhang, *Chinese Journal of Pharmacology and Toxicology*, 1988, 2(2): 98; Paulo A S. et al., *J. Biol. Chem.* 1996, 271: 23973); however, these natural FGAG also has platelet aggregation-inducing activity (Jia-zeng L. et al, *Thromb Haemos*, 1988, 54(3): 435; Chunwen Shan, *Pharmacology and Clinics of Chinese Materia Medica*, 1989, 5(3): 33).

FGAG has also been reported to have biological activities of regulation of blood lipid (His-Hisen L. et al., *J. Agic. Food Chem.*, 2002, 50: 3602), anti-artery atherosclerosis, and inhibition of vascular endothelial proliferation (Tapon-Bretaudiere et al., *Thromb. Haemost*, 2000, 84: 332; Masahiko I. et al., *Atherosclerosis*, 1997, 129:27; European patent application, EP 0811635), immunoregulation (Ling Sun et al., *Progress in biochemistry and biophysics*, 1991, 18 (5): 394; Zuqiong Chen et al., *Tianjin Medical Journal*, 1987, (5): 278), antineoplastic (Renjie Hu et al., *Chinese Journal of Clinical Oncology*, 1992, 19(1): 72; Weimin Li et al., *Journal of Clinical Oncology*, 1985, 12(2): 118) and antivirus (J A. Beutler et al., *Antivir. Chem. Chemother.*, 1993, 4(3), 167; PCT patent application PCT/JP90/00159), and so on.

Research data about antithrombotic activity, anticoagulant activity and action mechanisms and pharmacological targets of FGAG from sea cucumber and its derivatives show that FGAG has an anticoagulant mechanism that is different from that of heparin and dermatan sulfate, the targets of its anticoagulant/antithrombotic effect may relate to:

(1) AT-III: namely, there exists an AT-III-dependent antithrombin activity (Paulo A S et al., *J. Biol. Chem.*, 1996, 271, 23973; Xi Ma, *Chinese Journal of Hematology*, 1990, 11(5): 241); (2) HC-II: namely, there exists an HC-II-dependent antithrombin activity (Hideki Nagase et al., *Blood*, 1995, 85, (6):1527; Guangsen Zhang, *Chinese Journal of Hematology*, 1997, 18(3): 127); (3) IIa: namely, inhibiting feedback activation factor XIII of thrombin (IIa) (Nagase H et al., *Biochem. J.*, 1996, 119(1): 63-69); (4) f.xase: inhibiting the activation of factor X by endogenous factor Xase (factor VIII-IX complex) (Hideki Nagase et al., *Blood*, 1995, 85(6):1527; J P Sheehan et al., *Blood*, 2006, 107(10): 3876); (5) TFPI: increasing the rate of factor Xa inhibition by TFPI, reducing the inhibitory activity on TF-factor VIIa by TFPI-factor Xa, and stimulating the release of TFPI (Hideki Nagase et al., *Thromb Haemost*, 1997, 78: 864; T. Bretaudiere et al., *Thromb Haemost*, 2000, 84: 332); (6) plasmin: promoting plasminogen activation and thus promoting thrombolysis (Xiaoguang Yang et al., *Chinese Medical Sciences Journal*, 1990, 12(3), 187; Yutaka Kariya et al., *Biochem. J.*, 2002, 132: 335).

Although FGAG from sea cucumber has an important potential application value due to its unique anticoagulant mechanism and good anticoagulant activity intensity, so far FGAG is difficult to be used in clinical and this is mainly because:

(1) FGAG from sea cucumber has both anticoagulant activity and platelet aggregation-inducing activity. In clinical, the aim of anticoagulant is antithrombotic, and antiplatelet is another important approach to anti-thrombosis which is commonly used in clinical. Apparently, in terms of thrombosis, the anticoagulant activity for anti-thrombosis and the platelet-activating effect of promoting thrombosis of FGAG oppose each other, allowing it to be difficult to be used in clinical for preventing and treating hematologic diseases. For example, the studies indicate that in acute disseminated intravascular coagulation model of rabbits, the platelet-activating effect of FGAG from *Stichopus japonicas* entirely offsets its anticoagulant efficacy (Anguo Li, *Journal of Traditional Chinese Medicine University of Hunan*, 1991, 11(3): 37).

(2) Administration of pharmacodynamic dose of FGAG from *Stichopus japonicas* into the blood vessels of living animals can lead to platelet count reduction (Jiazeng Li, *Chinese Pharmacological Bulletin*, 1985, 6(2): 107). Thrombocytopenia, such as immune heparin-induced thrombocytopenia, may lead to hemorrhagic tendency or may lead to serious or even fatal disseminated intravascular coagulation. Available data show that platelet count reduction induced by FGAG from sea cucumber may be related to its platelet aggregation-inducing activity and thus "withhold" of the platelets in the microvascular (Jiazeng Li et al., *Bulletin of Chinese Materia Medic*, 1983, 8(5): 35).

(3) It is generally known that a wide range of pharmacological targets are closely related to the side effect of bleeding tendency of anticoagulant, and selective target has become an important evaluation index in the development of new anticoagulant drugs (K A Bauer, *Hematology*, 2006, (1): 450). FGAG from sea cucumber has different targets from that of the other anticoagulant drugs, however, as mentioned above, its targets are still relatively widespread. Available data show that an anticoagulant dose of FGAG can lead to significant bleeding tendency (Paulo A S et al., *British Journal of Haematology*, 1998, 101: 647).

Natural FGAG from sea cucumber has unique anticoagulant mechanism and potency, on the other hand has defects that limit its application. So, the acquisition of desired target products through structural modification has become one of the important contents of the application research.

At present, the methods for the chemical structural modification of FGAG comprise peroxide depolymerization (European patent disclosure, EP0408770; Ken-ichiro Y et al., *Tetrahedron Letters*, 1992, 33: 4959), desulfation or carboxyl reduction (Paulo A S et al., *Thrombosis Research*, 2001, 102: 167), partial acid hydrolysis (Yutaka Kariya, *Biochem. J.*, 2002, 132: 335; Paulo A S et al., Thrombosis Research, 2001, 102: 167), and etc. These efforts have made some progress. For example, studies show that the platelet aggregation-inducing activity of FGAG from *Stichopus japonicas* may weaken with the reduction of molecular weight (Huizeng Fan, *Journal of Biological Chemistry*, 1993, 9(2):146); AT-III-dependent antithrombin activity of the depolymerized product by peroxide of FGAG from *Stichopus japonicas* may also be reduced (Xi Ma, *Chinese Journal of Hematology*, 1990, 11(5): 241; Paulo A S et al., *J. Biol. Chem.* 1996, 271, 23973; Hideki Nagase et al., *Blood*, 1995, 85 (6):1527); For FGAG from *L. grisea*, the reduction of molecular weight has a more significant effect on HC-II-dependent antithrombin activity (R G Pacheco et al., *Blood Coagulation and Fibrinolysis*, 2000, 11:563).

By summarizing the research data about depolymerized product of FGAG (mostly referred to as DHG) from *Stichopus japonicas*, it is known that it is difficult to obtain anticoagulant active products with desired potency and target feature. For example, the data show that the platelet aggregation-inducing activity may be eliminated until the weight-average molecular weight of FGAG from *Stichopus japonicus* is reduced to 9000 Da (Huizeng Fan et al., *Journal of Biological Chemistry*, 1993, 9(2): 146); on the other hand, the anticoagulant activity weakens with the reduction of molecular weight (R G Pacheco et al., *Blood Coagulation and Fibrinolysis*, 2000, 11:563; Huizeng Fan et al., *Journal of Biological Chemistry*, 1993, 9(2): 146). According to the DHG-related pharmacological and pharmacodynamic research data, DHG with molecular weight less than 10000 Da was used in early, but in the subsequent more than ten years of research, weight-average molecular weight of DHG is mostly between 12000 and 15000 Da (Hideki Nagase et al., *Thromb Haemost*, 1997, 77(2): 399; Kazuhisa M et al., *Kidney International*, 2003, 63: 1548; J P Sheehan et al., *Blood*, 2006, 107(10): 3876). Apparently, the latter is required to maintain necessary anticoagulant potency, but for FGAG from *Stichopus japonicas*, the safety of this molecular weight range is in doubt in terms of eliminating platelet-inducing activity and avoiding intravascular administration-induced thrombocytopenia, and such safety has not been reflected and validated in the related research data.

Studies have shown that both hydrolysis and partial desulfation of fucose branches can significantly reduce or abolish anticoagulant activity of FGAG, reduction of carboxyl groups has relatively less effect on anticoagulant activity, but the bleeding tendency is still apparent and the effect on platelet activity is unknown (Paulo A S, *J. Biol. Chem.*, 1996, 271, 23973; Paulo A S et al., *British J. Haematology*, 1998, 101: 647; Paulo A S et al., *Thrombosis Research*, 2001, 102: 167).

Research data on chemical and biological activity of FGAG from sea cucumber mainly relates to FGAG from *L. grisea* and *Stichopus japonicas*. The extraction method of glycosaminoglycan from *Thelenota ananas* has been described (Xuexiang Liu et al., *Journal of Nanjing University of Traditional Chinese Medicine*, 2003, 19 (3): 161), but studies on its structure analysis and biological activity have not been reported.

It is seen from available data that the difference between structures of FGAG from *L. grisea* and *Stichopus japonicas* lies in the degree of sulfation. GalNAc backbones have different sulfated types and levels, and fucose branches have substantially the same type; while different types of fucose branches have different compositions and thus have different degrees of sulfation on branches (Ken-ichiro Y et al., *Tetrahedron Letters*, 1992, 33: 4959; Lubor Borsig et al. *J. Biol. Chem.* 2007, 282: 14984). According to the relative anticoagulant potency of such two FGAG compared to heparin and/or low molecular weight heparin, it is known that FGAG from *Stichopus japonicas* has stronger anticoagulant and antithrombotic potency (Norihiko S et al. *Thromb Haemost*, 1991, 65(4): 369; Paulo A S et al., *British J. Haematology*, 1998, 101: 647).

However, all the above efforts failed to illuminate the effect of platelet activation and intravenous administration of the obtained product on platelet count, which is the most important factor that limits the application value of FGAG from sea cucumber. Next, although the related documents reported the effect potency of these structure-modified products on certain blood factors (pharmacological targets), but the relationship between structural modification and features of pharmacological action mechanism of the obtained product is not clear. So far, the effect of sulfated position on the activity and action features of FGAG has not been reported. Alteration of sulfated type of the glycosyl groups on backbones and/or branches may obtain a new FGAG having more selective pharmacodynamic characteristics and thus having more application values, however, under the existing conditions, glycosaminoglycan can be treated by nonselective sulfation or defulfation, but it is difficult to be modified by position-selective sulfation or defulfation.

The present inventors find surprisingly by the comparative studies of the chemical structure and biological activity of FGAG from *Thelenota ananas* that the positions and types of fucose branches of FGAG have an important effect on the biological activity, especially on the platelet aggregation-inducing activity. Thus, FGAG from different species may have remarkable differences in application value. The present inventors also find that different depolymerization degrees and methods have different effects on the strength of biological effect that is produced by FGAG through different targets. Based on such difference, one can obtain the features with special target selectivity, and thus obtain FGAG derivatives for treating and/or preventing specific diseases.

The present inventors first find that fucosylated glycosaminoglycan from *Thelenota ananas* (THG) has special chemical structure features, and its fucose branch types are different to that of FGAG with known or partially known chemical structure, such as FGAG from *L. grisea* and *Stichopus japonicas*; THG also has special biological activities, and its platelet activation action is much lower than that of FGAG from such as *Holothuria leucospilota* and *Stichopus japonicas*.

The present invention demonstrates that THG has an activity of inhibiting endogenous factor X enzyme (f.Xase) and HC-II-dependent antithrombin (f.IIa), and first illuminates the relationship between the depolymerization degree of THG and the potency of the pharmacological action. Based on this, the present invention obtains depolymerized THG (dTHG) with higher ratio of f.Xase inhibition/anti IIa activity (potency ratio). Namely, based on the correlation rule between depolymerization and biological activity, the present invention obtains dTHG product with good anticoagulant potency and special target selectivity, starting from THG with special chemical and biological activity. Said dTHG has no platelet aggregation-inducing activity and does not cause platelet count reduction under conditions of high dose and repeated administration.

SUMMARY OF THE INVENTION

One object of the present invention is to provide a depolymerized glycosaminoglycan from *Thelenota ananas* (THG) with special chemical structure and good anticoagulant potency, which has no platelet aggregation-inducing activity and does not cause platelet count reduction.

Another object of the present invention is to provide a method for preparing the depolymerized glycosaminoglycan from *Thelenota ananas*.

Another object of the present invention is to provide a pharmaceutical composition containing the depolymerized glycosaminoglycan from *Thelenota ananas*, and its use for preparing medicines for prevention and/or treatment of thrombotic diseases.

The present invention finds that besides some known common features of FGAG, such as monosaccharide components including GalNAc, GlcUA, Fuc and etc., glycosaminoglycan from *Thelenota ananas* (THG) has special chemical structure features. Its fucose branch type and sulfation degree are different from that of the known or partially known FGAG from sea cucumber. For example, FGAG from *L. grisea* and *Stichopus japonicas* mainly comprise three types of fucose branches, i.e., -2,4-disulfated, -3,4-disulfated, and -4-sulfated fucoses, while THG mainly comprises -2,4-disulfated, -3-disulfated, and -4-sulfated fucoses.

Accordingly, the present invention demonstrates that THG has the activity of inhibiting endogenous factor Xase (f.Xase) and HC-II-dependent antithrombin (f.IIa) and finds that THG exhibits special feature in biological activity, such as having a much lower activity in platelet activation than FGAG from *Holothuria leucospilota* and *Stichopus japonicas*.

In addition, the present inventors find surprisingly by the comparative studies of the chemical structure and biological activity of THG that the positions and types of fucose branches of FGAG have an important effect on the biological activity, especially on the platelet aggregation-inducing activity.

Based on the above researches, the present invention obtains depolymerized THG (dTHG) product with good anticoagulant potency and special target selectivity, starting from THG with special chemical and biological activity, based on the correlation rule between depolymerization and biological activity.

According to one aspect of the present invention, said depolymerized THG (dTHG) is a depolymerized product of fucosylated glycosaminoglycan from *Thelenota ananas* (THG), having a structure shown in the following formula:

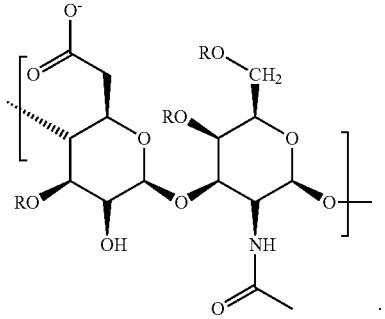

In formula (I): —OR represents hydroxyl groups (—OH), sulfate groups (—OSO$^{3-}$), or sulfated fucose residues shown as formula (II)

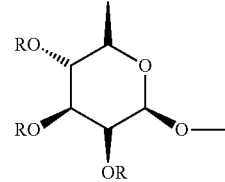

In formula (II): —OR represents the same as formula (I).

Wherein: monosaccharide components comprise N-acetyl galactosamine (GalNAc), glucuronic acid (GlcUA), fucose (Fuc), or sulfate thereof (—OSO$^{3-}$), based on molar ratio, GalNAc:GlcUA:Fuc:—OSO$^{3-}$ being about 1:(1±0.3):(1±0.3):(3.5±0.5); weight average molecular weight (Mw) of dTHG being about 8000~20000 Da. The molecular weight range is preferably 10000~18000 Da, and more preferably 12000~16000 Da.

Studies demonstrate that dTHG of the present invention has higher ratio of activity intensity (potency ratio) of anti f.Xase/anti f.IIa, higher potency ratio of antiXase/APTT extension, has no platelet aggregation-inducing activity and does not cause platelet count reduction under conditions of high dose and repeated administration, and thus can be used for the prevention and/or treatment of thrombotic diseases.

According to another aspect of the present invention, a method for preparing said depolymerized THG is provided, mainly comprising the following steps:

1) extraction: extracting and obtaining fucosylated glycosaminoglycan (THG) from the body wall of *Thelenota ananas*;

2) depolymerization: depolymerizing the THG obtained in step 1) to obtain depolymerized fucosylated glycosaminoglycan (dTHG);

3) purification: collecting and purifying dTHG with desired molecular weight to remove impurities with lower and/or higher molecular weight.

Particularly, step 1) generally may comprise the steps of cutting/grinding, enzymatic hydrolysis, alkaline hydrolysis, decolorization, separation. *Thelenota ananas* may be fresh or dry product without viscera. In order to increase the yield, said *Thelenota ananas* dried product is generally cut into flakes or small blocks and then immersed into water, while the fresh product may be cut and grinded directly by adding water into suspension, and then subjected to enzymatic and alkaline hydrolysis treatment.

In the step of enzymatic hydrolysis, broad-spectrum protease is generally selected, including such as pepsin, trypsin, complex enzyme or crude enzyme from animal; prolease such as papain, actinase from plant and/or microorganism. The enzymatic hydrolysis conditions such as temperature, time, pH and amount of enzyme may be determined according to the properties of the used prolease.

In the step of alkaline hydrolysis, strong alkali such as potassium hydroxide, sodium hydroxide may be used. Amount of alkali is selected to make the concentration of alkali in the extraction solution to be 0.5~2N (equivalent concentration), and reaction temperature may generally range from room temperature to 70° C., and alkali treatment time may be about 0.5~3 h.

The extraction solution after enzymolysis and/or alkali treatment is subjected to enzyme inactivation and neutralization, and then centrifugated and/or filtered to remove undissolved substances. The obtained supernatant may be treated or conjointly treated by a lower alcohol/ketone, such as ethanol, acetone; or a sylvite such as potassium acetate, or an acid mucopolysaccharide precipitant, such as cetylpyridinium precipitant to precipitate glycosaminoglycan in the solution. The obtained precipitant may be dried to get crude extract, or directly used in the next step without being dried. The obtained glycosaminoglycan crude extract may be purified by decolorization, fractional precipitation, gel permeation chromatography and/or ion exchange chromatography. Hydrogen peroxide decolorization combined with ehonal-potassium acetate fractional precipitation is preferably used in the present invention (see Huizeng Fan et al., *Pharmaceutical Journal,* 1983, 18 (3): 203) to obtain relatively purified fucosylated glycosaminoglycan from *Thelenota ananas*, i.e. THG.

In prevent invention, fucosylated glycosaminoglycan from *Thelenota ananas* (THG) shares some common features with known fucosylated glycosaminoglycan, such as monosaccharide components including acetyl galactosamine (GalNAc), glucuronic acid (GlcUA), fucose (Fuc) and etc., however, its degree of sulfation (expressed as $-OSO^{3-}$) is different from that of the known fucosylated glycosaminoglycan. Based on the integer (or half integer) molar ratio, the ratio of monosaccharide components and sulfate groups of GalNAc:GlcUA:Fuc:—$OSO^{3-}$ is close to 1:1:1:3.5, and particularly about 1:(1±0.3):(1±0.3):(3.5±0.5).

In step 2), depolymerization method of THG may select hydrogen peroxide depolymerization, or peroxide depolymerization catalyzed by the fourth period transition metal ions. The latter method is preferred in the present invention, which is described in detail in Chinese patent application No. 200910110114.0 entitled "Depolymerized Fucosylated Glycosaminoglycan And Preparation Method Thereof" submitted by the present applicant on Nov. 6, 2009. It employs a catalyst containing the fourth period transition metal ions in aqueous medium to catalyze peroxide depolymerization and obtain a depolymerized fucosylated glycosaminoglycan from *Thelenota ananas*. Particularly, the method comprises the following steps:

2.1) adding peroxide in aqueous medium in the presence of the fourth period transition metal ions to depolymerize fucosylated glycosaminoglycan from *Thelenota ananas* (THG);

2.2) stopping the reaction and collecting the depolymerized fucosylated glycosaminoglycan from *Thelenota ananas* (dTHG) within desired molecular weight range.

Wherein, the depolymerization is carried out in aqueous medium, peroxide can produce free radicals in the reaction system and degrade THG through a free radical chain reaction to generate dTHG product. Said peroxide includes but not limited to peracetic acid, hydrogen peroxide, 3-chloro-peroxybenzoic acid, hydrogen peroxide cumene, sodium persulfate, benzoyl peroxide, and a salt or an ester thereof. Hydrogen peroxide is preferred.

Said THG is about 0.05% to 15% based on the weight of the reaction system, and the peroxide is about 0.5% to about 30% based on the weight of the reaction system. During the depolymerization of FGAG, peroxide reactant may be added into the reaction system one-time before the reaction, and also may be added into the reaction system continuously or intermittently. Preferably, peroxide reactant is added into the reaction system continuously at a controlled rate in the present invention.

Said metal ion as catalyst is selected from the fourth period transition metal ions, including such as $Cu^+$, $Cu^{2+}$, $Fe^{2+}$, $Fe^{3+}$, $Cr^{3+}$, $Cr_2O_7^{2-}$, $Mn^{2+}$, $Zn^{2+}$, $Ni^{2+}$. These metal ions may be used alone or combined with each other as composite catalyst, wherein preferred catalyst may include $Cu^+$, $Cu^{2+}$, $Fe^{2+}$, $Fe^{3+}$, $Zn^{2+}$, and the most preferred is $Cu^{2+}$.

Because metal ion is not a self-existent chemical reagent, actually used is an inorganic or organic salt of the metal ions. In the reaction system, the concentration of said metal may be about 1 nmol/L~0.1 mol/L, and preferred concentration range is 10 μmol/L~10 mmol/L.

Said depolymerization reaction comprises the following conventional process parameters: temperature range is 10° C.~75° C.; reaction time is 20 min~8 h; the reaction may be carried out under atmospheric or pressurized conditions; may be carried out under inert gas such as nitrogen atmosphere, and also may be carried out under atmospheric conditions connected to atmospheric environment.

When the reaction finishes, a chelating agent may be optionally added into the reaction system to chelate with the metal ions to inhibit reaction rate, then by cooling, organic solvent precipitant and other techniques to stop the reaction. Chelating agent is a substance that combines with a metallic ion to form an inert chelate, including but not limited to, ethylenediamine tetraacetic acid (EDTA), diethylenetriamine pentaacetic acid (DTPA), 3-propylenediamine tetraacetic acid (PDTA), nitrilotriacetic acid (NTA), or a salt thereof. Disodium ethylenediamine tetraacetic acid or its hydrate is preferred in the method of the present invention. Reaction product precipitation is a method that precipitates polysaccharides from the reaction system by directly adding an organic solvent or further adding an inorganic salt (such as potassium acetate). Said organic solvent includes low-carbon alcohol/ketone, such as methanol, ethanol and acetone, and preferably is ethanol or acetone.

The above method can significantly improve the reaction condition of peroxide depolymerization of fucosylated glycosaminoglycan. That is, when employing the same peroxide reactant and original FGAG starting material to produce dFG with the same or approximately the same molecular weight and under the same temperature and other reaction conditions, this method can improve reaction rate, shorten reaction period, compared with direct peroxide depolymerization (namely the peroxide depolymerization method in the absence of metal ion catalyst). Similarly, under the condition of controlled reaction period, this method can significantly reduce the required reaction temperature, and even allow the reaction to proceed under room temperature.

During the repeated preparation of dTHG, under the same or similar reaction conditions, compared with direct peroxide depolymerization, the differences between different batches of the products obtained by this method is significantly reduced, the difference between the molecular weight of obtained depolymerized product and target molecular weight is less than 5%, significantly improving the repeatability and controllability of dTHG production, and make the depolymerized product have better quality uniformity. This may be related to relatively stable reaction rate due to the decrease of activation energy caused by catalyst, and may also be related to the moderate reaction conditions, such as lower reaction temperature and short reaction period, and the improvement of controllability and stability of reaction conditions.

In addition, in order to further enhance and improve the controllability of the depolymerization reaction, an inorganic and/or organic salt at a certain concentration may optionally be added to the peroxide depolymerization reaction system catalysted by metal ions. Said inorganic and/or organic salts includes a salt formed by a metal element (such as an alkali metal, an alkaline earth metal element) and halogen or organic acid; a salt formed by an organic acid or inorganic acid with an organic base, and combinations thereof. Sodium chloride, potassium chloride, sodium acetate, trihydrate sodium acetate, potassium acetate are preferred. In the present invention, preferred concentration of the inorganic and/or organic salts used to improve depolymerization rate and reaction controllability is about 0.1 mmol/L to about 1.0 mol/L.

In the present invention, the collected dTHG has a weight average molecular weight (Mw) of about 8000~20000 Da, preferably 10000~18000 Da, and more preferably 12000~16000 Da.

In step 3), the collected dTHG may be purified by a method known in the art to remove impurities with low and/or high molecular weight. Purification methods include but not limited to: dialysis method to remove low and/or high molecular weight impurities, ion-exchange method to produce a THG salt, and/or gel chromatography/anion exchange chromatography method.

The method of preparing depolymerized fucosylated glycosaminoglycan from *Thelenota ananas* of the present invention may further comprise the following step:

4) drying the dTHG obtained in step 3). Drying methods may be decompression vacuum drying or freeze drying. Freeze drying is preferably used in the present invention.

The ratio of monosaccharide components and sulfate groups of dTHG obtained by the above method of the present invention may be determined by the known methods in the art, such as chemical chromogenic method, infrared spectroscopy (IR) method, and nuclear magnetic resonance spectroscopy (NMR) method (Weijie Zhang, *Biochemical Study Techniques of Glycoconjugates* (Version 2), Zhejiang: Zhejiang University Press, 1999; Patent application of the present applicant mentioned above: CN200910110114.0).

Since the dTHG of the present invention has sulfate groups and carboxyl groups, it can be used with an inorganic ion or an organic alkaline group to form a pharmaceutically acceptable salt or ester. Said pharmaceutically acceptable salt or ester of dTHG may be an alkali metal and/or alkaline earth metal salt, preferably sodium salt, potassium salt or calcium salt. Apparently, these salts or esters should also included within the scope of the present invention.

According another aspect of the present invention, a pharmaceutical composition is provided, comprising dTHG of the present invention or a pharmaceutically acceptable salt or ester thereof, and pharmaceutically acceptable excipients. Said pharmaceutical composition may be formulated into various dosage forms, such as oral preparation (including solid and liquid preparation), injection preparation (including injection liquid and lyophilized powder for injection). However, the present inventors finds that of dTHG has poor oral absorption, but has good bioavailability when administrated by injection routes, such as subcutaneous injection. Thus, the pharmaceutical composition of the present invention is preferably formulated into injection preparation, and it can be formulated into a solution preparation and a freeze-dried product by conventional techniques in the art because dTHG has good water solubility.

Said dTHG of the present invention is potent endogenous factor Xase inhibitor, and has good anticoagulant and antithrombotic activity, thus the above pharmaceutical composition containing dTHG can be used for the prevention and/or treatment of thrombotic diseases, such as the treatment of various postoperative anticoagulation, prevention and treatment of various arteriovenous thrombus, prevention and treatment of thrombus-related cardiovascular and cerebrovascular diseases. Usage and dosage for the prevention and/or treatment of different diseases should be decided by clinical doctors.

DETAILED DESCRIPTION OF THE INVENTION

Figure 1:
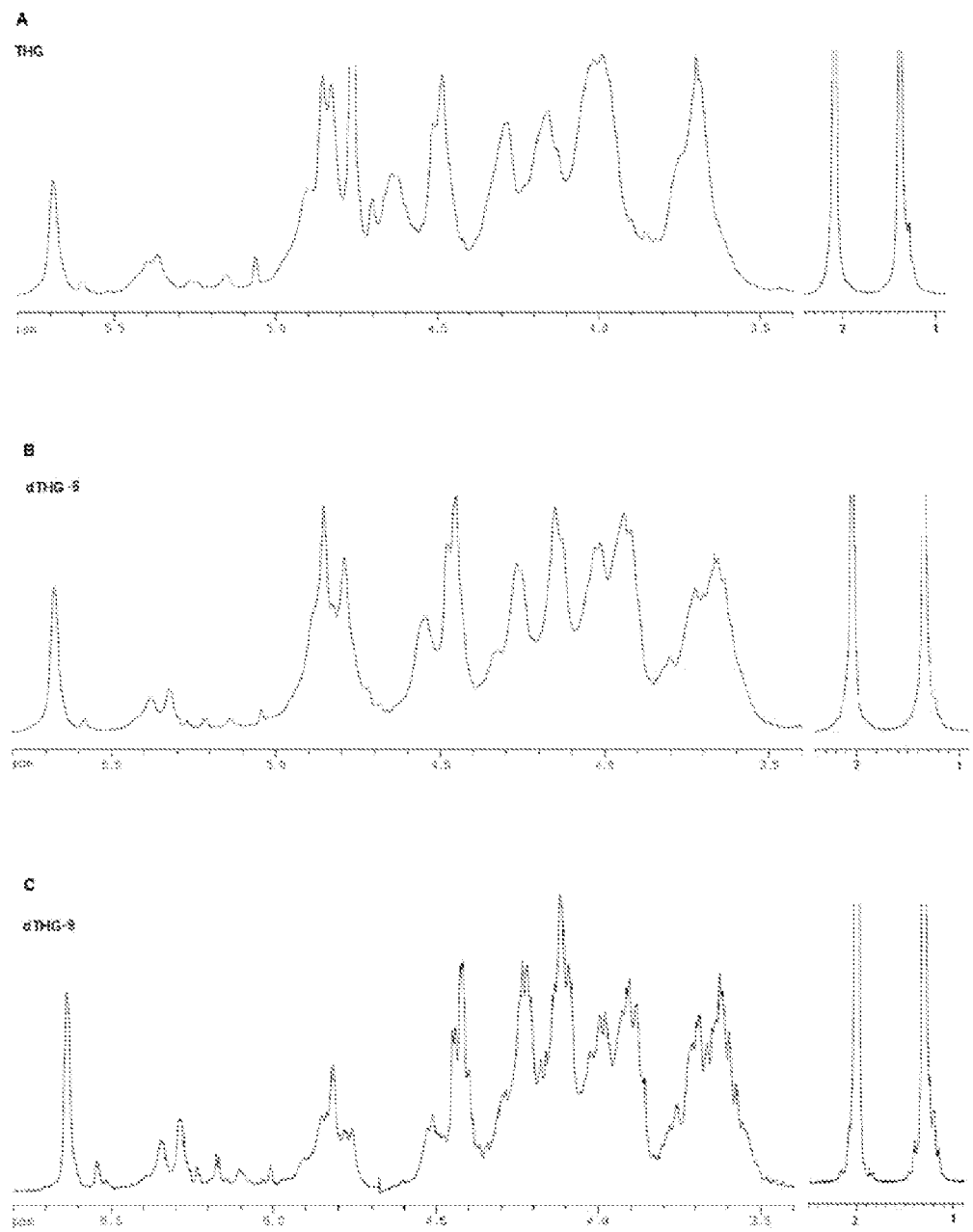
FIG. 1: shows $^1$H NMR spectroscopies of THG and dTHG samples, wherein the water peaks in the spectroscopies of dTHG-6 and dTHG-9 are suppressed.

The present invention can be further understood through the following detailed description of the examples in conjunction with the accompanying drawings. The examples should not be construed to limit the scope of the present invention.

Example 1

Extraction, Depolymerization and Purification of THG 1.1 Materials

*Thelenota ananas*, commercially available, viscera removal and body wall dried

*Stichopus japonicas*, commercially available, viscera removal and body wall dried

*H. leucospilota*, commercially available, viscera removal and body wall dried.

Papain: $8 \times 10^5$ U/g, available from Guangxi Nanning Pangbo Biological Engineering Co., Ltd.

Cation exchange resin: 001×7 strongly acidic styrene type cation exchange resin, available from Nankai University Resin Co. Ltd. (Tianjin).

Reagents such as KOH, KCOCH$_3$, H$_2$O$_2$, and ethanol were commercially available analytical reagents.

1.2 Extraction 20 kg dry *Thelenota ananas* were cut with slicer into sheets with a thickness of about 1.5 mm, placed into a laminated reaction vessel (300 L), added with 200 L water, stirred and soaked, and then added with solid NaOH under stirring until the concentration of NaOH reached 0.5M. Alkaline hydrolysis reaction was carried out at 60° C. for 2 h. The reactants were cooled, adjusted to pH 6~7 with 6N HCl, and added with 100 g of papain. The reaction was carried out at 50° C. for 6 h under stirring and then heated to 100° C. maintaining for 10 min. The reactants were cooled, adjusted to pH 2 with 6N HCl (to precipitate proteins), placed at 2~8° C. for about 4 h, and centrifugated to remove precipitate. The resultant supernatant was adjusted to about pH 7, added with ethanol until reaching a final concentration of 70%, and then still placed and centrifugated. The centrifuged precipitate was dissolved in 30 times (v/v) of water, centrifugated to remove undissolved substances, adjusted to about pH 10 with 2M NaOH, and added with H$_2$O$_2$ until reaching a final concentration of about 3% (v/v), and then reacted at 50° C. for 2 h (decolourization). The reaction solution was added with potassium acetate until reaching a final concentration of 0.5 mol/L, and added with ethanol until reaching a final concentration of 30%. The solution was then still placed and centrifugated. The centrifuged precipitate was dissolved in 20 times (v/w) of water, centrifugated to remove undissolved substances, added with potassium acetate until reaching a final concentration of 2.5 mol/L, placed still and centrifugated. The centrifuged precipitate was washed twice with ethanol, and the residual ethanol was removed under reduced pressure. The precipitate was dissolved in water and then frozen-dried to obtain 162 g of fucosylated glycosaminoglycan from *Thelenota ananas* (THG).

As controls, 2 kg of *Stichopus Japonicus* and *Holothuria leucospilota* were respectively extracted under the above conditions and 20.2 g of FGAG from *Stichopus Japonicus* (SJG) and 15.6 g of FGAG from *Holothuria leucospilota* (HLG) were obtained respectively.

1.3 Depolymerization and Purification 50 g of THG obtained by the above method was added into 1825 ml of water containing 122 g of sodium acetate trihydrate and 60 g of NaCl, and added with 120 ml of 0.0668 mol/L copper acetate solution, and mixed well under stirring. Under stirring condition in 35° C. water bath, 10% (V/V) H$_2$O$_2$ was dropwised at the rate of 126 ml/h in about 2 h. During the whole process, pH of the reaction system was controlled at 7.2~7.8. The reaction was carried out under above conditions for about 5 h. During the reaction, about 180 ml of reaction solution was taken at the point of 0.2, 0.5, 1.0, 1.5, 2.0, 2.5, 3.0, 3.5, 4.0, 4.5 and 5.0 h after the start of the reaction, respectively.

Each of the reaction solution was added with 0.5 g of Na$_2$EDTA immediately after taking, adjusted to pH 6.5-7.0 with 15% acetic acid, then added with ethanol, 2.5 times the volume of the reaction solution (about 450 ml), placed still and centrifugated to obtain precipitate. The precipitate was dissolved with 100 ml of water, and precipitated again with ethanol (250 ml of 95% ethanol). The centrifuged precipitate was washed twice with 50 ml of ethanol, and ethonal was removed under reduced pressure. The precipitate was dissolved with 30 times volume (v/v) of water, filtrated through a 0.45 μm membrane. The filtrate was passed through Na$^+$ type cation exchange resin column (Ø 40 mm×250 mm), the eluent was collected and dialyzed for 6 h using a 3500-Da molecular weight cut-off dialysis membrane. The dialyzed cut-off solution was frozen-dried to obtain depolymerized products corresponding to each depolymeriztion time point dTHG-1~dTHG-10. Amounts of product at each time point were about 3.0~3.5 g, with a total amount of 33.2 g.

As controls, 10 g SJG and 10 g HLG were respectively taken and depolymerized under the same conditions as mentioned above. Two time points of taking the depolymerization reaction solution were set, i.e., 3 h and 5 h after the start of reaction. The obtained depolymerized products were designated as dSJG-1, dSJG-2 and dHLG-1, dHLG-2. The total amount of dSJG was 7.5 g, and the total amount of dHLG was 8.0 g, 1.3 Determination and Comparison of Physical and Chemical Properties of dTHG, dSJG and dHLG Sample: THG, dTHG-1~dTHG-10

Control sample: SJG, dSJG-1~dSJG-3; HLG; dHLG-1~dHLG-4

Detection of molecular weight: HPGPC-LALLS

Detection of optical rotation: Chinese pharmacopoeia (2005) part II, appendix VI E method. WZZ-1S automatic polarimeter, sodium lamp ($\lambda_{589.3nm}$), sample cell 1 dm Detection of intrinsic viscosity: Chinese pharmacopoeia (2005) part II, appendix VI G, method 3

Detection of Monosaccharide Components:

Acetylgalactosamine (GalNAc): Elson-Morgon method (Weijie Zhang, Biochemical Study Techniques of Glycoconjugates (Version 2), Zhejiang: Zhejiang University Press, 1999, 409-410)

Glucuronic acid (GluUA): Carbazole method;

Fucose (Fuc): calculation of the molar ratio of GalNAc/Fuc according to integral area of methyl peaks of said $^1$H NMR in example 2

Sulfate group (—OSO$^{3-}$): detection of the molar ratio of carboxylic acid/sulfuric acid by conductance method (Weijie Zhang, *Biochemical Study Techniques of Glycoconjugates* (Version 2), Zhejiang: Zhejiang University Press, 1999, 409-410) as the ratio of components GlcUA/—OSO$^{3-}$ Results: see Table 2.

TABLE 2

Chemical components and physical and chemical properties of each sample

| Sample | Molecular weight (Mw) | Optical rotation ($[\alpha]_D^{20}$, C = 1%) | Intrinsic viscosity (0.1M NaCl, ml/g) | Monosaccharide components (molar ratio) GalNAc:GlcUA:Fuc:—OSO$_3^-$ |
|---|---|---|---|---|
| THG | 65820 | −59.1° | 46.7 | 1.00:1.16:1.01:3.60 |
| dTHG-1 | 46070 | −58.3° | 29.3 | 1.00:1.09:1.00:3.52 |
| dTHG-2 | 33260 | −58.2° | 19.2 | 1.00:1.12:1.02:3.61 |

TABLE 2-continued

Chemical components and physical and chemical properties of each sample

| Sample | Molecular weight (Mw) | Optical rotation ($[\alpha]_D^{20}$, C = 1%) | Intrinsic viscosity (0.1M NaCl, ml/g) | Monosaccharide components (molar ratio) GalNAc:GlcUA:Fuc:—$OSO_3^-$ |
|---|---|---|---|---|
| dTHG-3 | 25380 | −59.5° | 13.5 | 1.00:1.03:0.98:3.45 |
| dTHG-4 | 19650 | −57.3° | 9.64 | 1.00:1.06:1.01:3.50 |
| dTHG-5 | 17150 | −55.7° | 8.07 | 1.00:1.15:0.97:3.42 |
| dTHG-6 | 13950 | −53.7° | 6.17 | 1.00:1.03:0.96:3.53 |
| dTHG-7 | 11580 | −58.4° | 4.84 | 1.00:1.08:1.00:3.48 |
| dTHG-8 | 10260 | −55.9° | 4.12 | 1.00:1.04:0.99:3.56 |
| dTHG-9 | 8549 | −59.0° | 3.25 | 1.00:1.06:0.97:3.55 |
| dTHG-10 | 6725 | −56.9° | 2.37 | 1.00:1.01:0.95:3.43 |
| SJG | 68740 | −64.2° | 54.6 | 1.00:1.05:1.02:4.12 |
| dSJG-1 | 14930 | −63.5° | 16.9 | 1.00:0.98:0.95:4.09 |
| dSJG-2 | 9300 | −60.3° | 8.5 | 1.00:0.95:0.93:3.93 |
| HLG | 51500 | −48.9° | 36.5 | 1.00:0.97:0.89:2.01 |
| dHLG-1 | 13320 | −47.3° | 5.70 | 1.00:0.97:0.85:1.98 |
| dHLG-2 | 9790 | −47.6° | 4.24 | 1.00:0.95:0.84:1.96 |

It can be seen from the results of table 2, the molar ratios of GalNAc:GlcUA:Fuc in dTHG, dSJG, dHLG and in their original polysaccharides THG, SJG, HLG were approximately equal to 1:1:1, while the contents of sulfated groups were different, in which the content in SJG/dSJG is higher, and the content in HLG/dHLG is lower. In addition, the optical rotation and intrinsic viscosity between FGAG from the three sources had relatively large differences.

For THG/dTHG, the change of the ratio of monosaccharide components in the product produced by the same batches of sea cucumber was small, while in THG and/or dTHG produced by different batches of raw materials, the ratio of the above monosaccharide components changed in a wide range. Generally, the molar ratio of GalNAc:GlcUA:Fuc:—$OSO_3^{3-}$ was within the range of 1:(1±0.3):(1±0.3):(3.5±0.5).

It also can be seen from above results that in the product obtained by peroxide depolymerization catalyzed by transitional metal ions, the ratio of the content of fucose to sulfate group changed little, and it is known by $^1$H-$^1$H COSY analysis that the reducing end of the product was mainly GalNAc, which was substantially identical with the conclusion of the above patent application CN200910110114.0 of the present applicant.

Example 2

Spectrum Analysis of THG and dTHG

Sample: THG, dTHG-6, dTHG-9, with the same sources as Example 1

Control sample: SJG, SJG-1, with the same sources as Example 1

Detection spectrum: $^1$H NMR; $^1$H-$^1$H COSY; $^1$H-$^1$H TOCSY; $^1$H-$^1$H NOESY; $^{13}$C-NMR; DEPT-135°; $^1$H-$^{13}$C HSQC; $^1$H-$^{13}$C HMBC Detection condition: solvent: $D_2O$, 99.9 Atom % D (Norell company); internal standard, trimethylsilyl-propionic acid (TSP-d4); temperature, 45° C.

Instrument: AVANCE AV 400 Superconducting Nucleus Magnetic Resonance Spectrometer (400 MHz, Bruker, Switzerland)

Spectrum: see FIG. 1~FIG. 4.

Result Analysis:

(1) Comparison of the Spectroscopies of THG and dTHG:

FIG. 1 shows $^1$H NMR spectroscopies of THG, dTHG-6, dTHG-9, wherein the water peaks in the spectra of dTHG-6 and dTHG-9 were suppressed. It can be seen from FIG. 1 that THG, dTHG-6 and dTHG-9 had substantially identical signal features, only when the molecular weight was lower, the signal was more distinct. It is seen that the NMR signal features kept stable before and after depolymerization of THG, and the basic chemical structures had no significant change before and after depolymerization of THG.

Figure 2:
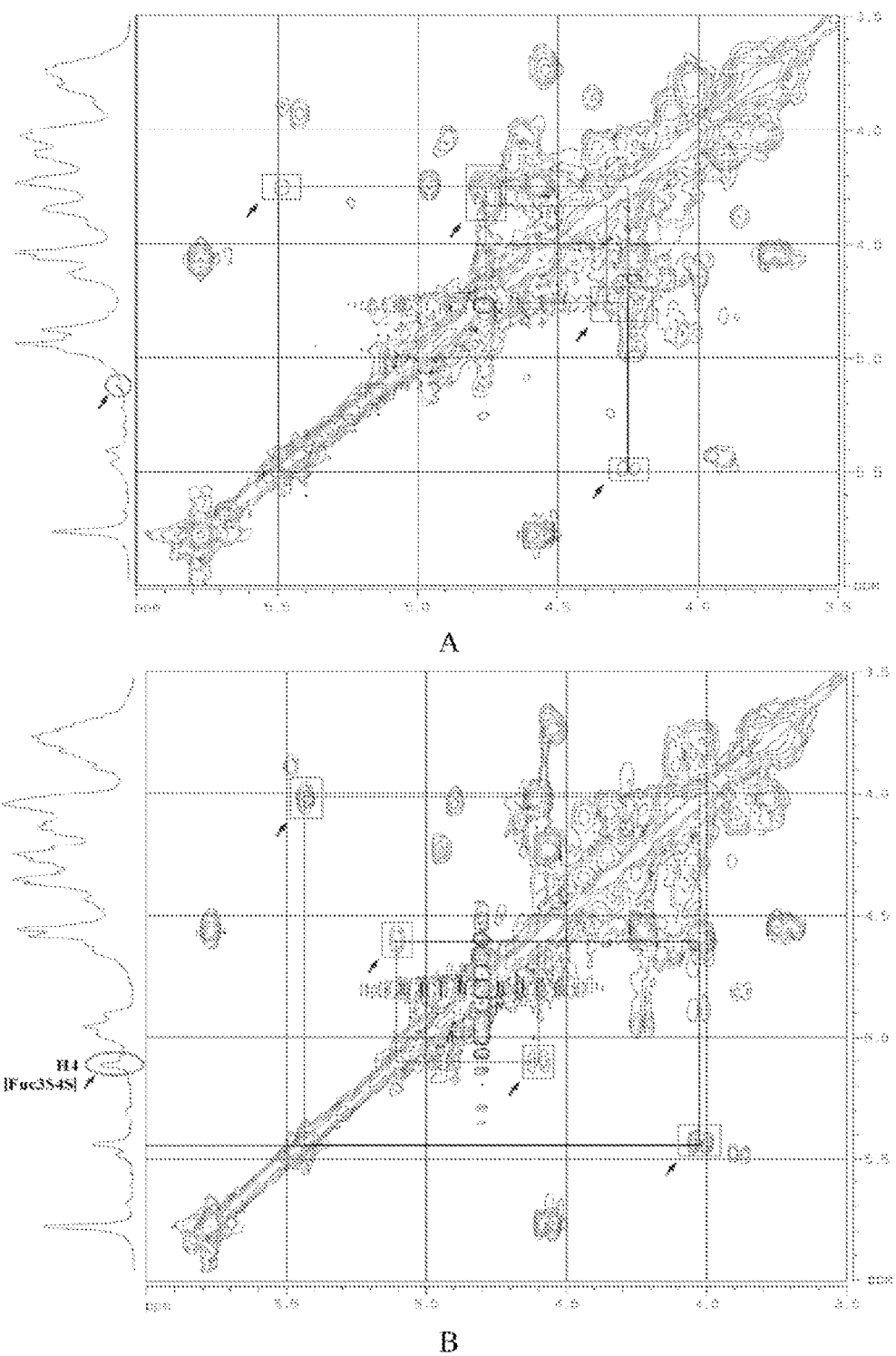
FIG. 2: shows $^1$H-$^1$H COSY spectroscopies of dTHG (A) and depolymerized FGAG from *Stichopus Japonicus* (i.e., dSJG, B); wherein signals indicated by arrows show the differences in the structure of fucose branches between the two depolymerized FGAG: FIG. A shows the related signals of 3-sulfated fucose of dTHG; FIG. B shows the related signals of 3,4-disulfated fucose of dSJG; signals in panes are respectively the related hydrogen signals of 3-sulfated fucose and 3,4-disulfated fucose; signals in the two circles are the signals of H-4 position of 3,4-disulfated fucose.
Figure 3:
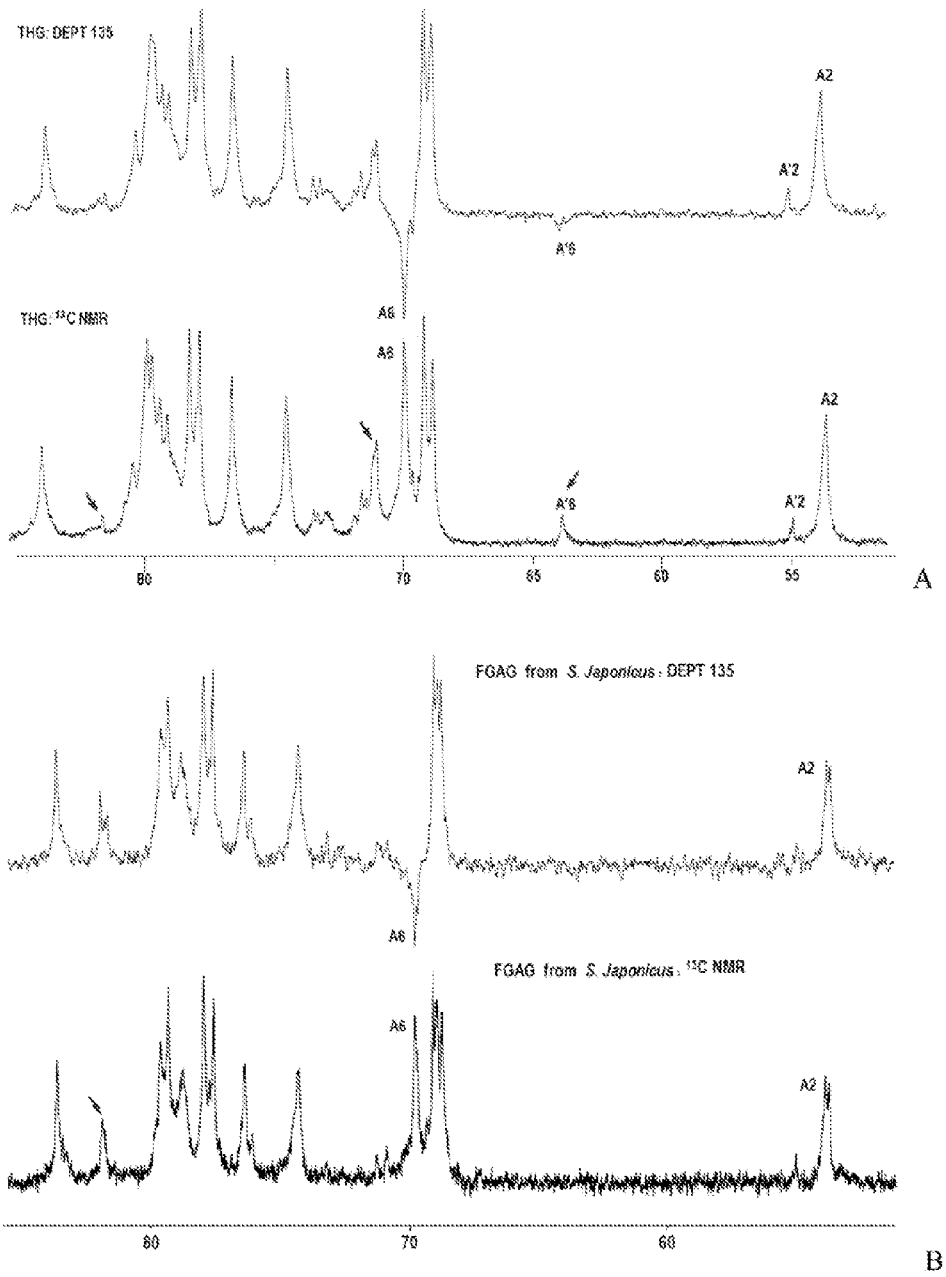
FIG. 3: shows $^{13}$C NMR and DEPT spectroscopies of THG and FGAG from *Stichopus Japonicus* (i.e., SJG)
Figure 4:
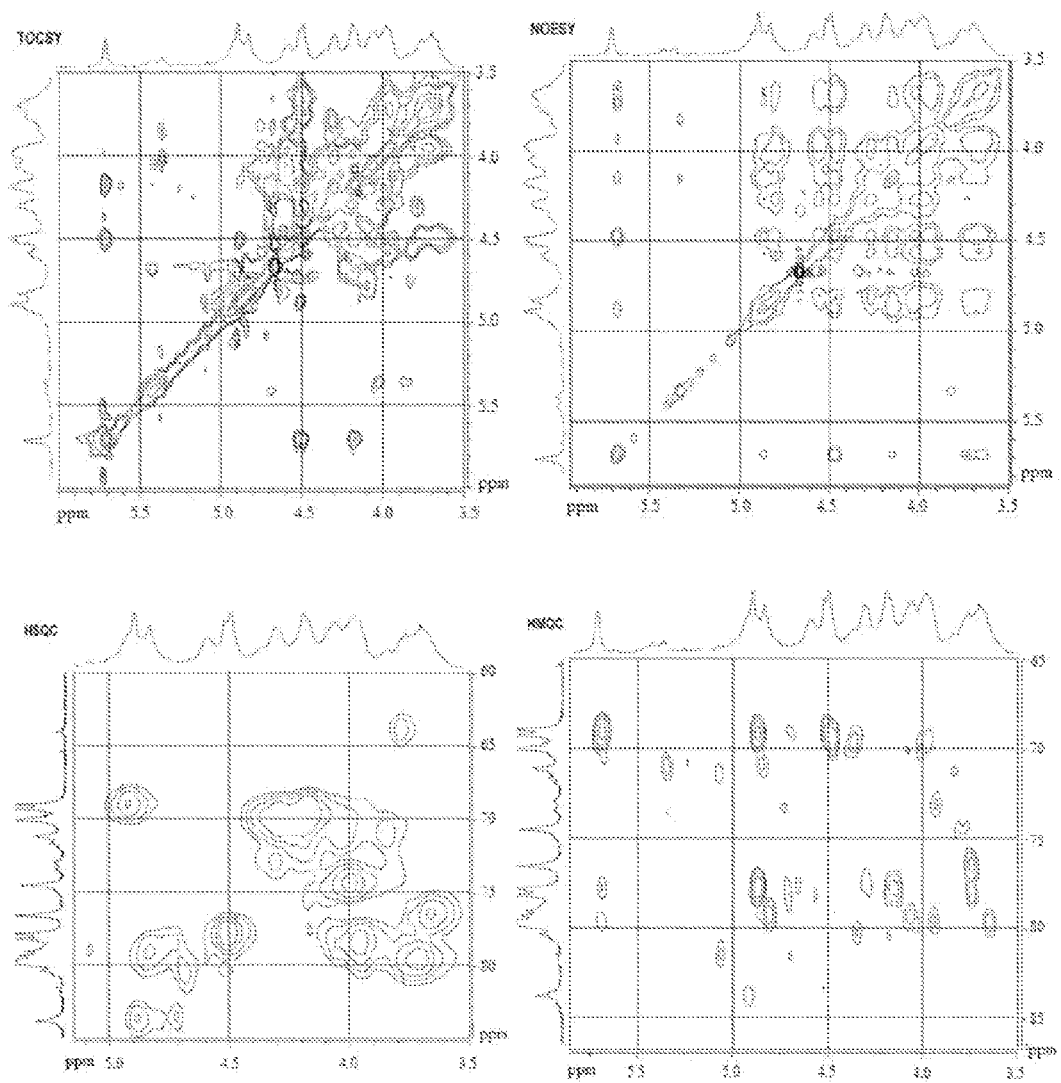
FIG. 4: NMR homonuclear/heteronuclear correlation spectroscopies of dTHG-6.

(2) Comparison of the Spectroscopies of THG and SJG:

With reference to FIG. 2~FIG. 4, FIG. 2 shows $^1$H-$^1$H COSY spectroscopies of dTHG (A) and dSJG (B); wherein signals indicated by arrows show the differences in the structure of fucose branches between the two depolymerized FGAG: FIG. A shows the related signals of 3-sulfated fucose of dTHG; FIG. B shows the related signals of 3,4-disulfated fucose of dSJG; signals in panes are respectively the related hydrogen signals of 3-sulfated fucose and 3,4-disulfated fucose; signals in the two circles are the signals of H-4 position of 3,4-disulfated fucose. FIG. 3: shows $^{13}$C NMR and DEPT spectra of THG and SJG. FIG. 4 shows NMR homonuclear/heteronuclear correlation spectra of dTHG-6.

It can be seen by summarizing the spectrum data that THG and SJG had substantially the same backbone structure, and the distinct difference between them lied in: as shown in FIG. 2, strong signal of 3,4-disulfated fucose of dSJG was weak or did not occur in the spectroscopy of THG; and the signal belonging to 3-sulfated fucose of THG did not occur in the spectroscopy of SJG, indicating that they had significant difference in the substituent type on branches.

With reference to FIG. 3, carbon signals of GalNAc having and having no sulfate substituent at 6-position occurred at about 70 ppm and about 64 ppm respectively. Due to C-6 position of GalNAc being a secondary carbon, its signal peak in DEPT 135° spectroscopy was a negative peak. It can be seen from FIG. 3, there was still small amount of GalNAc (less than 10%) whose hydroxyl groups at C-6 positions was not substituted by sulfate groups in the backbone of THG, while there substantially existed no GalNAc whose C-6 positions was not substituted by sulfate groups in the backbone of SJG. This further demonstrated that there was difference between the substituent groups on branches of THG and SJG.

In addition, as can be seen from the existing literature, there was difference in the substituent on branches between THG of present invention and the other known FGAG from sea cucumber. For example, the references (Paulo A S et al., *J. Biol. Chem.* 1996, 271: 23973; Lubor Borsig et al., *J. Biol. Chem.* 2007, 282, 14984) and the accompanying $^{13}$C NMR spectroscopy showed that about 35% of GalNAc in FGAG from *L. grisea* were not substituted by sulfate groups at C-6 position. Reference (Huizeng Fan, et al., *Pharmaceutical Journal*, 1980, 18(3): 203) showed that the backbone GalNAc of FGAG from *Holothuria leucospilota* only had 6-position sulfation and not 4-position sulfation.

To sum up, THG of the present invention has chemical structure, which differed from the known structures of FGAG from other species. Firstly, it has different substituent types on fucose branches, namely mainly comprising -2,4-disulfated, -3-sulfated, and -4-sulfated fucose, while had no or little -3,4-disulfated fucose; and its backbone was different to some extend from FGAG from other source.

(3) Data and Assignment of NMR Spectroscopies of dTHG-6: See Table 3 for Assignment of the Spectroscopy, see FIG. 4 for Several Relevant Spectroscopy.

TABLE 3

Data and assignment of $^1$H/$^{13}$C-NMR spectroscopies of THG-6

| Position assignment | | $^1$H NMR δ [ppm] | Correlated hydrogen shown in spectroscopies | | | $^{13}$C NMR δ [ppm] | DEPT 90/135° | Correlated hydrogen shown in spectroscopies | |
|---|---|---|---|---|---|---|---|---|---|
| | | | COSY | TOCSY | NOESY | | | HMQC | HMBC |
| GalNAc 4S6S (A) | 1 | 4.45 | 2$^#$ | 2$^#$, 3$^#$ | 3$^#$, 4$^#$, 5$^#$, U3$^#$ | 102.5 | CH | 1$^#$ | 2$^#$, 3$^#$, U-4$^#$ |
| | 2 | 4.04 | 1$^#$, 3$^#$ | 1$^#$, 3$^#$, 4$^#$ | — | 54.1 | CH | 2$^#$ | 1$^#$, 3$^#$ |
| | 3 | 3.93 | 2$^#$, 4$^#$ | 2$^#$, 4$^#$ | 1$^#$, 4$^#$, 5$^#$ | 78.2 | CH | 3$^#$ | 1$^#$, 2$^#$, 4$^#$, 5$^#$ |
| | 4 | 4.82 | 3$^#$, 5$^#$ | 3$^#$, 5$^#$ | 1$^#$, 3$^#$, 5$^#$, 6$^#$, 6$^{'#}$ | 79.4 | CH | 4$^#$ | 3$^#$, 4$^#$, 6$^#$, |
| | 5 | 3.97 | 4$^#$, 6$^#$, 6$^{'#}$ | 4$^#$, 6$^#$, 6$^{'#}$ | 4$^#$, 5$^#$, 6$^#$, 6$^{'#}$ | 74.6 | CH | 5$^#$ | |
| | 6 | 4.23 | 5$^#$, 6$^{'#}$ | 5$^#$, 6$^{'#}$ | 3$^#$, 4$^#$, 5$^#$, 6$^{'#}$ | 69.3 | CH$_2$ | 6$^#$ 6$^{'#}$ | 5$^#$, 6$^{'#}$ |
| | 6' | 4.11 | 5$^#$, 6$^#$ | 5$^#$, 6$^#$ | 3$^#$, 4$^#$, 5$^#$, 6$^#$ | | | | |
| | 7 | / | / | / | / | 177.7 | C | / | 2$^#$, 8$^#$ |
| | 8 | 2.01 | / | / | 1$^#$, 3$^#$, 4$^#$, 5$^#$ | 25.4 | CH$_3$ | 8$^#$ | 8$^#$ |
| GalNAc 4S (A') | 1 | 4.51 | 2$^#$ | 2$^#$, 3$^#$ | [3$^#$, 4$^#$], 5$^#$ | 102.5 | CH | 1$^#$ | |
| | 2 | 3.91 | 1$^#$, 3$^#$ | 1$^#$, 3$^#$ [4$^#$] | / | 55.3 | CH | 2$^#$, 3$^#$ | |
| | 3 | 3.80 | 2$^#$, 4$^#$ | [2$^#$, 4$^#$] | [—] | 78.2 | CH | 3$^#$ | |
| | 4 | 4.76 | 3$^#$, 5$^#$ | [3$^#$, 5$^#$] | [—] | 80.4 | CH | 4$^#$ | |
| | 5 | 3.73 | 4$^#$, 6$^#$, 6$^{'#}$ | 4$^#$, [6$^#$, 6$^{'#}$] | [4$^#$, 5$^#$, 6$^#$, 6$^{'#}$] | 74.6 | CH | 5$^#$ | 4$^#$, 6$^#$ |
| | 6 | 3.62 | 5$^#$, 6$^{'#}$ | [5$^#$, 6$^{'#}$] | [3$^#$, 4$^#$, 5$^#$, 6$^{'#}$] | 64.1 | CH$_2$ | 6$^#$ 6$^{'#}$ | |
| | 6' | 3.69 | 5$^#$, 6$^#$ | [5$^#$, 6$^#$] | [3$^#$, 4$^#$, 5$^#$, 6$^#$] | | | | |
| | 7 | / | / | / | / | 177.7 | C | / | 2$^#$, 8$^#$ |
| | 8 | 1.98 | / | / | [1$^#$, 3$^#$, 4$^#$, 5$^#$] | 25.4 | CH$_3$ | 8$^#$ | 8# |
| GlcUA (U) | 1 | 4.42 | 2$^#$ | 2$^#$, 3$^#$, 4$^#$, 5$^#$ | 3$^#$, 5$^#$ | 106.6 | CH | 1$^#$ | 2$^#$, 3$^#$, A-3$^#$, |
| | 2 | 3.57 | 1$^#$, 3$^#$ | 1$^#$, 3$^#$, 4$^#$, 5$^#$ | 4$^#$ | 74.7 | CH | 2$^#$ | 3$^#$ |
| | 3 | 3.71 | 2$^#$, 4$^#$ | 1$^#$, 2$^#$, 4$^#$, 5$^#$ | 1$^#$, 5$^#$ | 79.9 | CH | 3$^#$ | 2$^#$, 4$^#$ |
| | 4 | 3.90 | 3$^#$, 5$^#$ | 1$^#$, 2$^#$, 3$^#$, 5$^#$ | 2$^#$ | 79.1 | CH$_3$ | 4$^#$ | 5$^#$ |
| | 5 | 3.66 | 4$^#$ | 1$^#$, 2$^#$, 3$^#$, 4$^#$ | 3$^#$, 1$^#$ | 79.6 | CH | 5$^#$ | 4$^#$ |
| | 6 | / | / | / | / | 177.7 | C | / | 4$^#$, 5$^#$ |
| Fuc-2S4S (I) | 1 | 5.64 | 2$^#$ | 2$^#$, 3$^#$ | 2$^#$, U3$^#$ | 99.2 | CH | 1$^#$ | U-3$^#$ |
| | 2 | 4.45 | 1$^#$, 3$^#$ | 1$^#$, 3$^#$, 4$^#$ | 1$^#$ | 76.5 | CH | 2$^#$ | 1$^#$, 3, 4$^#$ |
| | 3 | 4.09 | 2$^#$, 4$^#$ | 1$^#$, 2$^#$, 4$^#$ | 4$^#$, 5$^#$, 6$^#$ | 69.3 | CH | 3$^#$ | 1$^#$, |
| | 4 | 4.84 | 3$^#$, 5$^#$ | 3$^#$, 5$^#$ | 3$^#$, 5$^#$, 6$^#$ | 83.8 | CH | 4$^#$ | 5$^#$, 6$^#$ |
| | 5 | 4.90 | 4$^#$, 6$^#$ | 4$^#$, 6$^#$ | 3$^#$, 4$^#$, 6$^#$ | 69.0 | CH | 5$^#$ | 4$^#$ |
| | 6 | 1.31 | 5$^#$ | 4$^#$, 5$^#$ | 3$^#$, 4$^#$, 5$^#$ | 18.6 | CH$_3$ | 6$^#$ | 5$^#$, 6$^#$ |
| Fuc-3S (II) | 1 | 5.36 | 2$^#$ | 2$^#$, 3$^#$ | 2$^#$, U3$^#$ | 101.3 | CH | 1$^#$ | 2$^#$ |
| | 2 | 4.13 | 1$^#$, 3$^#$ | 1$^#$, 3$^#$, 4$^#$ | 1$^#$ | 73.3 | CH | 2$^#$ | |
| | 3 | 4.60 | 2$^#$, 4$^#$ | 1$^#$, 2$^#$, 4$^#$ | 4$^#$, 5$^#$, 6$^#$ | 83.8 | CH | 3$^#$ | 4$^#$ |
| | 4 | 4.18 | 3$^#$, 5$^#$ | 3$^#$, 5$^#$ | 3$^#$, 5$^#$, 6$^#$ | 71.9 | CH | 4$^#$ | 3$^#$ |
| | 5 | 4.47 | 4$^#$, 6$^#$ | 4$^#$, 6$^#$ | 3$^#$, 4$^#$, 6$^#$ | 69.7 | CH | 5$^#$ | 3$^#$, 4$^#$ |
| | 6 | 1.31 | 5$^#$ | 4$^#$, 5$^#$ | 3$^#$, 4$^#$, 5$^#$ | 18.6 | CH$_3$ | 6$^#$ | 6$^#$ |
| Fuc-4S (III) | 1 | 5.28 | 2$^#$ | 2$^#$, 3$^#$ | 2$^#$, U3$^#$ | 101.2 | CH | 1$^#$ | |
| | 2 | 3.80 | 1$^#$, 3$^#$ | 1$^#$, 3$^#$ | 1$^#$ | 71.1 | CH | 2$^#$ | 1$^#$, 2$^#$ |
| | 3 | 3.99 | 2$^#$, 4$^#$ | 1$^#$, 2$^#$, 4$^#$ | 4$^#$, 5$^#$, 6$^#$ | 71.2 | CH | 3$^#$ | 4$^#$, 5$^#$ |
| | 4 | 4.78 | 3$^#$, 5$^#$ | 3$^#$, 5$^#$ | 3$^#$, 5$^#$, 6$^#$ | 83.8 | CH | 4$^#$ | 5$^#$, 6$^#$ |
| | 5 | 4.80 | 4$^#$, 6$^#$ | 4$^#$, 6$^#$ | 3$^#$, 4$^#$, 6$^#$ | 69.0 | CH | 5$^#$ | 4$^#$ |
| | 6 | 1.31 | 5$^#$ | 5$^#$ | 3$^#$, 4$^#$, 5$^#$ | 18.0 | CH$_3$ | 6$^#$ | 5$^#$, 6$^#$ |

In the above table, GalNAc4S6S represents 4,6-disulfated-N-acetyl galactosaminyl; GalNAc4S represents 4-sulfated-N-acetyl galactosaminyl; Fuc-2S4S represents 2,4-disulfated fucose; Fuc-3 represents 3-sulfated fucose; Fuc-4S represents 4-sulfated fucose; Fuc-0S represents unsulfated fucose; bracket [ ] represents data undetermined due to overlapping signals.

Example 3

Detection of Biological Activities of THG/dTHG 3.1 Detection of Platelet Inducing Activity Sample: dTHG-1~dTHG-10, with the same source as example 1

Control sample: dSJG-1~dSJG-4, with the same source as example 1

Method: New Zealand white rabbit was taken blood from abdominal aorta. The blood was antifreezed with 3.8% sodium citrate (1:9) and centrifugated at 200×g for 8 min to get platelet-rich plasma (PRP), and centrifugated at 1500×g for 10 min to get platelet-poor plasma. Platelet count of PRP is about $4.0 \times 10^5/mm^3$. Bron method (Born G V R. *Nature*, 1962, 194:927): The effect of the samples on platelet aggregation was detected with platelet aggregometer. In the experiment, physiological saline was used as blank control, and the final concentration of the sample was 200 μg/ml. The experiment was repeated for 3 times and the mean values of maximum degree of platelet aggregation were calculated.

Results: see Table 4.

3.2 Detection of Anticoagulant Activity In Vitro

Sample: dTHG-1~dTHG-10, with the same sources as Example 1

Control sample: dSJG-1~dSJG-4; with the same sources as Example 1

Low molecular weight heparin sodium (LMWH): 3500-5500 Da, 0.4 ml×4000AxaIU, Anofi Aventis (France)

Reagent: thrombase (IIa): 123 NTH U/mg, Sigma (USA)

Chromogenic substrate of thrombase testing (S): 25 mg/vial, HYPHEN BioMed (France)

Heparin Cofactor II (HC-II): 100 μg/vial, HYPHEN BioMed (France)

Factor VIII (f.VIII): 200 IU/vial, Green Cross (China) Biological Products Co., LTD F.VIII Assay Kit: reagents comprise: Reagents: R1: Human Factor X; R2: Activation Reagent, human Factor IXa, containing human thrombin, calcium and synthetic phospholipids; R3: SXa-11, Chromogenic substrate, specific for Factor Xa; R4:Tris-BSA Buffer; HYPHEN BioMed (France).

Rabbit platelet-poor plasma: Guangzhou Rui Special Biological Technology Co., Ltd.

APTT assay kit (gallogen): Shanghai Sun Biological Technology Co., Ltd.

Apparatus: microplate reader, Bio-Rad 680 (USA), BICO Two Channel Coagulometer, Minivolt (Italy)

TABLE 4

Comparison of platelet aggregation-inducing activity of different FGAG

| Sample | NS | THG | dTHG-1 | dTHG-2 | dTHG-3 | dTHG-4 |
|---|---|---|---|---|---|---|
| Platelet aggregation rate | 2.7 ± 4.1 | 28.1 ± 7.8 | 16.3 ± 5.6 | 12.8 ± 4.9 | 9.3 ± 4.8 | 3.9 ± 2.8 |
| Sample | dTHG-5 | dTHG-6 | dTHG-7 | dTHG-8 | dTHG-9 | dTHG-10 |
| Platelet aggregation rate | 1.9 ± 2.9 | 1.1 ± 1.3 | 2.9 ± 3.3 | 2.4 ± 3.3 | 1.2 ± 2.5 | 3.4 ± 4.3 |
| Sample | SJG | dSJG-1 | dSJG-2 | HLG | dHLG-1 | dHLG-2 |
| Platelet aggregation rate | 58.4 ± 13.6 | 22.7 ± 8.5 | 5.3 ± 5.5 | 53.6 ± 17.4 | 18.3 ± 8.6 | 4.6 ± 5.4 |

By comparing the platelet inducing activity of the above FGAG from *Thelenota ananas, Stichopus japonicas* and *Holothuria leucospilota* and the depolymerized product with different depolymerization degrees, it can be found that for original FGAG, the platelet aggregation-inducing activity of THG was far lower than that of SGJ and HLG, indicating that the structural difference of FGAG from different sources had a great effect on the platelet activity. Since the structure difference of THG, SJG and HLG mainly lied in the type difference of sulfated fucose branches, thus it is presumed that the difference of platelet activity attributes to the difference of fucose branches. The type/feature of fucose branches of THG effectively weakened its platelet aggregation activity. From the molecular weight, when the weight average molecular weight of THG was decreased to about 20000 Da, the platelet aggregation activity of dTHG disappeared, while only when the molecular weight of SJG and HLG decreased to about 9000-12000 Da, the platelet activation effect under high concentration may be avoided. This substantially coincided with the conclusion of the reference (Huizeng Fan, et al., *Journal of Biological Chemistry*, 1993, 9(2): 146), indicating that dTHG has better application value than original THG.

Method:

(1) Detection of the activity of inhibiting intrinsic factor Xase (f.Xase, Tenase): The detection method established by f.VIII assay kit and f.VIII reagent was used. 30 μl of a series of known concentration of THG, dTHG, SJG, LMWH solution or blank control solution (Tris-BSA buffer solution $R_4$) was mixed with 1.0 IU/ml factor VIII (30 μl), then sequentially added with reagent kit $R_2$ (30 μl), $R_1$ (30 μl), and incubated at 37° C. for 1 min, then added with $R_3$ (30 μl) and incubated at 37° C. for 1 min, and added with 20% acetic acid (60 μl) to stop the reaction and $OD_{405nm}$ was detected. ΔOD was calculated based on the blank control ($R_4$), and $IC_{50}$ of the inhibition of f.Xase of each sample was calculated by the formula provided in the reference (Sheehan J. P. & Walke E. K., *Blood*, 2006, 107:3876-3882).

(2) Detection of HC-II-dependent anticoagulant activity: 50 μl of a series of the concentration of THG, dTHG, SJG, LMWH solution or blank control solution (Tris-BSA buffer solution $R_4$) was added to a 96 well enzyme marking plate, added and mixed with 50 μl of 1 μmol/L HC-II, incubated at 37° C. for 2 min, then added with 50 μl of 5 U/ml IIa and incubated at 37° C. for 2 min, then added and mixed with 50 μl of 2 mmol/l CS-0138, incubated at 37° C. for 1 min, and added with 50% acetic acid (100 μl) to stop the reaction and $OD_{405nm}$ was detected. ΔOD was calculated based on the blank control (R4), and $IC_{50}$ of the inhibition of IIa of each sample was calculated by the formula provided in the reference (Sheehan J. P. & Walke E. K., *Blood,* 2006, 107:3876-3882).

(3) Detection of the activity of extending APTT time: 10 μl of a series of the concentration of THG, dTHG, SJG, LMWH solution or blank control solution (Tris-buffer solution $R_4$) was mixed to 180 μl of rabbit plasma, then the APTT time of each sample was detected according to the method of the kit. The drug concentration for multiplying APTT time (double APTT time) was calculated according to the detection result of each sample.

Figure 5:
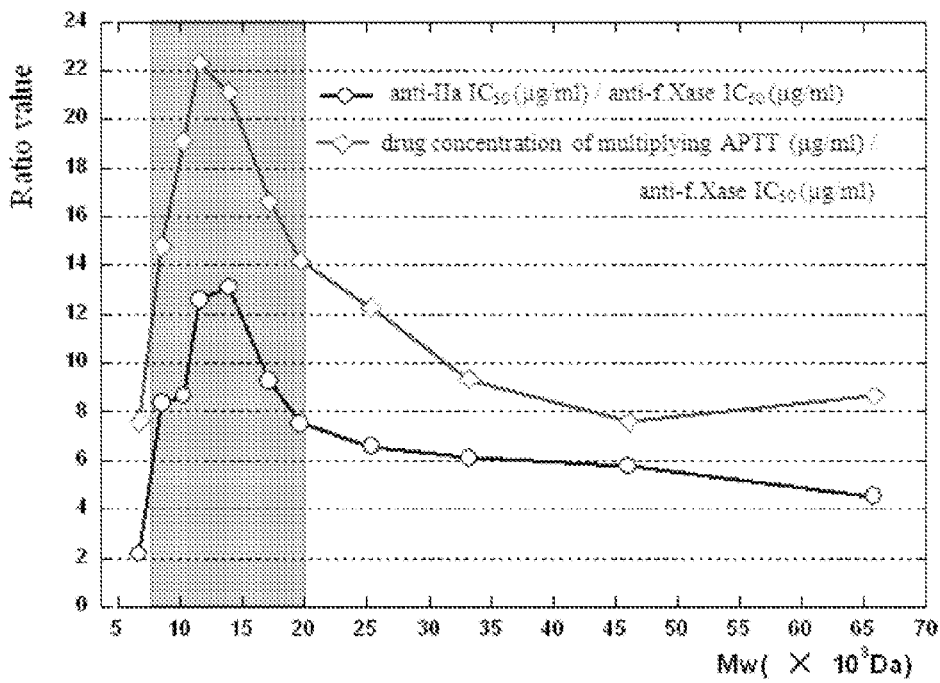
FIG. 5: shows the relationship of the potency of the inhibition of f.Xase activity, HC-II-dependent anti-IIa activity and the extension of APTT time, wherein the part defined in pane is the molecular weight of dTHG of the present invention.

Results: see Table 5 and FIG. 5.

it still had anticoagulant activity (extending APTT time). Obviously, dTHG in the molecular weight range possibly had better application value compared to original THG.

Secondly, both THG and dTHG had strong activity of inhibiting endogenous f.Xase. Under the condition mentioned in Example 3.2 of the present invention, dTHG (or THG) with a weight-average molecular weight of about 8000~70000 Da generally had an $IC_{50}$ of inhibiting f.Xase of less than about 0.1 μmol/L (less than about 1 μg/ml), and exhibited an enhanced tendency with the increase of the molecular weight. However, the tendency had large difference in different molecular weight range. When the molecular weight was less than about 12000 Da, the f.Xase-inhibitory activity of dTHG may distinctly weakened with the decrease of the molecular weight; while when the molecular weight

TABLE 5

Anticoagulant activitiy of THG/dTHG and control sample

| Sample | Molecular weight Mw (Da) | $IC_{50}$ (μg/ml) Anti-f.Xase | $IC_{50}$ (μg/ml) Anti-IIa | Potency ratio of anti-f.Xase-anti-IIa [1] | Drug concentration for multiplying APTT (μg/ml) | Potency ratio of anti-f.Xase-extension of APTT [2] |
|---|---|---|---|---|---|---|
| THG | 65820 | 0.275 | 1.25 | 4.54 | 1.77 | 8.66 |
| dTHG-1 | 46070 | 0.270 | 1.56 | 5.78 | 2.05 | 7.59 |
| dTHG-2 | 33260 | 0.268 | 1.64 | 6.11 | 2.50 | 9.32 |
| dTHG-3 | 25380 | 0.266 | 1.75 | 6.58 | 3.28 | 12.3 |
| dTHG-4 | 19650 | 0.253 | 1.90 | 7.51 | 3.59 | 14.2 |
| dTHG-5 | 17150 | 0.245 | 2.27 | 9.26 | 4.08 | 16.6 |
| dTHG-6 | 13950 | 0.216 | 2.84 | 13.1 | 4.56 | 21.1 |
| dTHG-7 | 11580 | 0.282 | 3.55 | 12.6 | 6.29 | 22.3 |
| dTHG-8 | 10260 | 0.463 | 4.02 | 8.68 | 8.82 | 19.1 |
| dTHG-9 | 8549 | 0.714 | 5.96 | 8.34 | 10.6 | 14.8 |
| dTHG-10 | 6725 | 0.864 | 6.23 | 2.17 | 21.9 | 7.6 |
| SJG-2 | 9300 | 0.683 | 5.35 | 7.83 | 9.7 | 14.2 |
| LMWH | 3500~5500 | 9.22 | 6.08 | 0.66 | 4.48 | 0.48 |

[1] Potency ratio of anti-f.Xase-anti-IIa: anti-IIa $IC_{50}$ (μg/ml)/anti-f.Xase $IC_{50}$ (μg/ml)
[2] Potency ratio of anti-f.Xase- APTT extension: drug concentration of multiplying APTT (μg/ml)/anti-f.Xase $IC_{50}$ (μg/ml)

The literatures (G Z. Feuerstein, et al., *Arterioscler Thromb Vasc Biol.,* 1999, 19:2554; C. J. Refino, et al., *Arterioscler Thromb Vasc Biol.,* 2002, 22:517) showed that f.IXa inhibitor may substantially inhibit the formation of thrombus under the dosage of without effecting blood APTT and bleeding time, and bleeding tendency of the anticoagulant was associated with the activity of antithrombin. In addition, clinical trial with low molecular heparin had confirmed that with the improvement of potency ratio of anti Xa/anti IIa, its bleeding tendency was significantly decreased (G. Andriuoli et al. *Heamostasis,* 1985, 15: 324). Based on above knowledge and the relationship between molecular weight of dTHG and its potency on different blood coagulation factor targets, appropriate depolymerization of THG may eliminate platelet aggregation-inducing activity of FGAG, but also produce potency ratio of anti f.Xase and HC-II-dependent anti IIa activity as high as possible, and/or potency ratio of anti f.Xase and/or extending APTT activity as high as possible.

The results of Table 5 showed that THG and/or dTHG had the activities of extending APTT time, inhibiting intrinsic f.Xase and HC-II dependent antithrombase. Depolymerization of THG may eliminate its platelet inducing activity, but the depolymerization degree had different effect on its activities of anti f.Xase, anti IIa (HC-II-dependent) and the extension of APTT.

Firstly, when the molecular weight (Mw) of dTHG was decreased to 20000 Da, its platelet inducing activity disappeared completely, and when Mw was decreased to 6000 Da, was not less than about 12000 Da, the $IC_{50}$ is in the range of about 0.2 μg/ml~0.3 μg/ml, based on molar concentration, the $IC_{50}$ may slightly decrease with the increase of the molecular weight; but based on mass concentration, the $IC_{50}$ substantially did not change with the molecular weight, or more exactly, it slightly increased with the increase of the molecular weight. As a whole, when dTHG (or THG) had a molecular weight of no less than about 10000 Da, its endogenous f.Xase-inhibitory activity may maintain constant to some extent.

The results of Table 5 also showed that THG/dTHG has activities of HC-II-dependent antithrombin and extending APTT time. For dTHG (or THG) with a molecular weight of about 8000~70000 Da, both the activity of HC-II-dependent antithrombin and the activity of extending APTT time enhanced with the increase of the molecular weight, which were manifested in the liner decrease of $IC_{50}$ of HC-II-dependent antithrombin activity and drug concentration of multiplying APTT time with the increase of logarithm value of molecular weight.

It is concluded by summarizing the above results according to the present invention that when dTHG had a molecular weight of more than about 10000 Da, especially about 12000 Da, the molecular weight had an effect on extending APTT time and HC-II-dependent antithrombin activity of dTHG, which was much larger than the effect on inhibiting endogenous f.Xase activity. For the convenience of description, "potency ratio of anti-f.Xase-anti-IIa" and "potency ratio of anti-f.Xase-APTT extension" were defined in Table 5 to reflect the features of anticoagulant activity of THG/dTHG with different molecular weight. As a whole, for dTHG with a molecular weight of no less than 10000 Da, the lower the molecular weight was, the higher the potency ratio of the f.Xase inhibitory activity to HC-II-dependent antithrombin activity or APTT time extension was. When the molecular weight was more lower (less than about 10000 Da), the potency ratio exhibited a decreased tendency.

The results of Table 5 also showed that LMWH had a relatively weak anti-f.Xase activity, and platelet induction activity of dSJG limited the application of the product with a stronger activity and/or higher "potency ratio". Based on the features of (1) eliminating platelet induction activity, (2) achieving a high anti-Xase/anti-IIa potency ratio as possible, and/or (3) achieving a high anti-Xase/APTT extension potency ratio, the present invention comprehensively pondered the relationship between the molecular weight of dTHG and f.Xase inhibitory activity, HC-II-dependent anti-thrombin activity, APTT time-extending activity and platelet effect. The dTHG selected according to the present invention may have a weight-average molecular weight (Mw) of about 8000~20000 Da, preferably about 10000~18000 Da, more preferably about 12000~16000 Da.

3.3 Resistance of dTHG to Venous Thrombosis

Sample: dTHG-6, with the same sources as Example 1; Low molecular weight heparin sodium (LMWH): 3500~5500 Da, 0.4 ml×4000AxaIU, Anofi-Aventis Method:

(1) Venous thrombosis in rabbit: A male New Zealand white rabbit was narcotized with pentobarbital, the bilateral jugular veins were separated and respectively placed two ligation sutures at 2 cm segment, and intravenously injected with recombinant human tissue factor at a dose of 1 ng/kg. The proximal end and distal end of the vein were ligated after 5 min, and the blood vessel was longitudinally cut after 15 min to take out thrombus. Residual blood was sucked with a filter paper, and wet weight of the thrombus was weighed. Test drugs (dTHG-6, LMWH) and control solvent (physiological saline, NS) were all administered subcutaneously before 2 hours of vein ligation.

(2) Detection of bleeding time: A SD rat was narcotized with pentobarbital (30 mg/kg ip), and intravenously injected with dTHG-6 or LMWH. After 15 seconds, its tail was cut off (5 mm from the end of the tail). Bleeding from the amputated tail was sucked at every 15 second with filter paper. No bleeding for continuous 1 min was considered as bleeding-stopping.

Results:

(1) Venous thrombosis in rabbit: In the model of venous thrombosis under the conditions of ligation and hyperviscosity, subcutaneous injection of dTHG-6 at 4.5, 9, 18 mg/kg could substantially inhibit thrombosis, and the inhibition rate ranged about 35% to about 70%. The inhibition activity exhibited distinct dose-effect relationship (Table 6). In this experiment, had the inhibition rate of LMWH at 720 IU/kg on venous thrombosis was about 56%

TABLE 6

Effect of THG on jugular vein thrombosis

| Group | | n | Weight of thrombus (mg) | Inhibition rate (%) |
|---|---|---|---|---|
| Model group | | 10 | 152.8 ± 13.6 | — |
| THG | 4.5 mg/kg | 10 | 98.3 ± 25.6* | 35.7 |

TABLE 6-continued

Effect of THG on jugular vein thrombosis

| Group | | n | Weight of thrombus (mg) | Inhibition rate (%) |
|---|---|---|---|---|
| | 9 mg/kg | 10 | 56.4 ± 20.6* | 63.1 |
| | 18 mg/kg | 10 | 45.7 ± 26.8* | 70.1 |
| LMWH | 720 IU/kg | 10 | 67.3 ± 21.2* | 56.0 |

Compared with the model group:
*P < 0.05,
**P < 0.01

Figure 6:
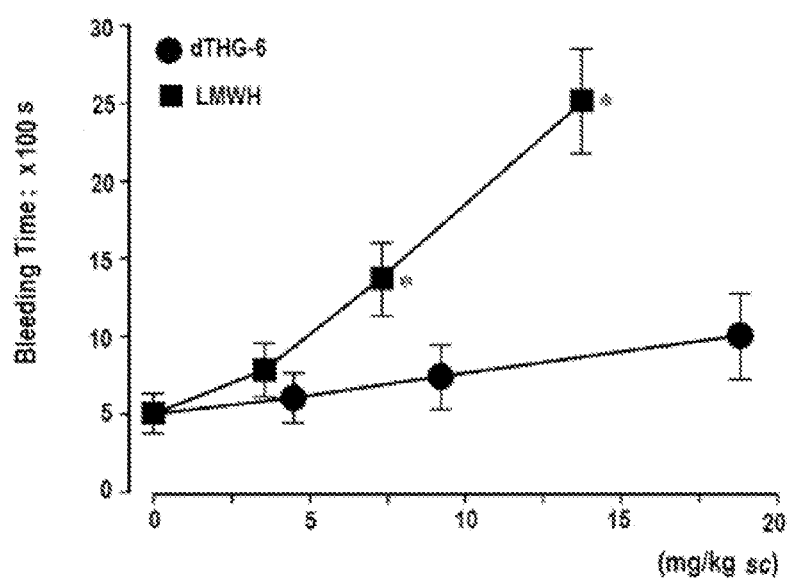
FIG. 6: shows the effect of dTHG and low molecular weight heparin (LMWH) on bleeding time in animals.

(2) Detection of bleeding time: The detection results of the effect of subcutaneous injection of dTHG-6 or LMWH on bleeding time in rat were shown in FIG. 6. The experimental results showed that compared with LMWH, under the similar anticoagulant and antithrombotic disage, dTHG-6 had a lower effect on bleeding time.

What is claimed is:

1. A depolymerized glycosaminoglycan from *Thelenota ananas* and a pharmaceutically acceptable salt thereof, said depolymerized glycosaminoglycan from *Thelenota ananas* comprising a depolymerized product of fucosylated glycosaminoglycan from *Thelenota ananas*, which has a weight average molecular weight of 8000 to 20000 Da, has monosaccharide components of N-acetyl galactosamine, glucuronic acid, fucose and their sulfates, and has a molar ratio between N-acetyl galactosamine:glucuronic acid:fucose:sulfate —$OSO_3$ of $1:(1\pm0.3):(1\pm0.3):(3.5\pm0.5)$.

2. The depolymerized glycosaminoglycan from *Thelenota ananas* and a pharmaceutically acceptable salt thereof according to claim 1, wherein the sulfated fucose comprises 3-sulfate-fucose.

3. The depolymerized glycosaminoglycan from *Thelenota ananas* and a pharmaceutically acceptable salt thereof according to claim 1, wherein said depolymerized glycosaminoglycan from *Thelenota ananas* has a weight average molecular weight of 10000 to 18000 Da.

4. A method for preparing a depolymerized glycosaminoglycan from *Thelenota ananas* and a pharmaceutically acceptable salt thereof, according to claim 1, comprising the steps of:
   1) extracting and obtaining fucosylated glycosaminoglycan from the body wall of *Thelenota ananas*;
   2) depolymerizing the fucosylated glycosaminoglycan obtained in step 1) by peroxide depolymerization to obtain an depolymerized fucosylated glycosaminoglycan; and
   3) collecting and purifying the depolymerized fucosylated glycosaminoglycan with a desired molecular weight.

5. The method according to claim 4, wherein said fucosylated glycosaminoglycan from *Thelenota ananas* is depolymerized in an aqueous medium in the presence of a catalyst to obtain the depolymerized fucosylated glycosaminoglycan, said catalyst is a catalyst containing a metal ion selected from the group consisting of the fourth period transition metals in the periodic table.

6. The method according to claim 5, wherein said catalyst containing a metal ion selected from the group consisting of the fourth period transition metals in the periodic table is an inorganic salt or an organic salt of $Cu^+$, $Cu^{2+}$, $Fe^{2+}$, $Fe^{3+}$, $Cr^{3+}$, $Cr_2O_7^{2-}$, $Mn^{2+}$, $Zn^{2+}$, $Ni^{2+}$, or the combination thereof.

7. A pharmaceutical composition comprising the depolymerized glycosaminoglycan from *Thelenota ananas* or a pharmaceutically acceptable salt thereof according to claim 1, and pharmaceutically acceptable excipients.

8. The pharmaceutical composition according to claim 7, wherein said pharmaceutically acceptable salt is sodium, potassium or calcium salt.

9. The pharmaceutical composition according to claim 7, wherein said pharmaceutical composition is formulated into freeze-dried powder for injection.

10. A method of treating a thrombotic disease, comprising administering an effective amount of the pharmaceutical composition according to claim 7 to a subject in need thereof.

11. A pharmaceutical composition comprising the depolymerized glycosaminoglycan from *Thelenota ananas* or a pharmaceutically acceptable salt thereof according to claim 2, and pharmaceutically acceptable excipients.

12. A pharmaceutical composition comprising the depolymerized glycosaminoglycan from *Thelenota ananas* or a pharmaceutically acceptable salt thereof according to claim 3, and pharmaceutically acceptable excipients.

13. The pharmaceutical composition according to claim 11, wherein said pharmaceutically acceptable salt is sodium, potassium or calcium salt.

14. The pharmaceutical composition according to claim 12, wherein said pharmaceutically acceptable salt is sodium, potassium or calcium salt.

15. The pharmaceutical composition according to claim 8, wherein said pharmaceutical composition is formulated into freeze-dried powder for injection.

16. The pharmaceutical composition according to claim 11, wherein said pharmaceutical composition is formulated into freeze-dried powder for injection.

17. The pharmaceutical composition according to claim 12, wherein said pharmaceutical composition is formulated into freeze-dried powder for injection.

18. The pharmaceutical composition according to claim 13, wherein said pharmaceutical composition is formulated into freeze-dried powder for injection.

19. The pharmaceutical composition according to claim 14, wherein said pharmaceutical composition is formulated into freeze-dried powder for injection.

20. A method of treating a thrombotic disease, comprising administering an effective amount of the pharmaceutical composition according to claim 8 to a subject in need thereof.

* * * * *